United States Patent
Zargari et al.

(10) Patent No.: US 8,410,068 B2
(45) Date of Patent: Apr. 2, 2013

(54) COMPOUNDS FOR THE TREATMENT OR ALLEVIATION OF EDEMA, AND METHODS FOR THEIR USE

(75) Inventors: Arezou Zargari, Solna (SE); Lars-Goran Axelsson, Tierp (SE); Ann-Kristin Spiik, Tullinge (SE); Nikolai Kouznetsov, Jarfalla (SE)

(73) Assignee: Index Pharmaceuticals AB, Stockholm (SE)

( * ) Notice: Subject to any disclaimer, the term of this patent is extended or adjusted under 35 U.S.C. 154(b) by 147 days.

(21) Appl. No.: 12/681,590

(22) PCT Filed: Oct. 2, 2008

(86) PCT No.: PCT/SE2008/000542
§ 371 (c)(1),
(2), (4) Date: Apr. 2, 2010

(87) PCT Pub. No.: WO2009/045145
PCT Pub. Date: Apr. 9, 2009

(65) Prior Publication Data
US 2010/0240736 A1     Sep. 23, 2010

Related U.S. Application Data

(60) Provisional application No. 60/978,010, filed on Oct. 5, 2007.

(51) Int. Cl.
| | | |
|---|---|---|
| A01N 43/04 | (2006.01) | |
| C12P 19/34 | (2006.01) | |
| C12Q 1/68 | (2006.01) | |
| C07H 21/02 | (2006.01) | |
| C07H 21/04 | (2006.01) | |

(52) U.S. Cl. .......... 514/44; 435/6; 435/91.1; 435/91.31; 435/455; 536/23.1; 536/24.5

(58) Field of Classification Search .............. 435/6, 91.1, 435/91.31, 455; 514/1, 2, 44; 536/23.1, 536/24.5

See application file for complete search history.

(56) References Cited

U.S. PATENT DOCUMENTS

| | | | |
|---|---|---|---|
| 5,968,826 A | 10/1999 | Bennett et al. | |
| 6,610,836 B1 | 8/2003 | Breton et al. | |
| 6,900,301 B2 | 5/2005 | Cook et al. | |
| 7,517,644 B1 * | 4/2009 | Smith | 435/6.12 |
| 7,618,814 B2 * | 11/2009 | Bentwich | 435/320.1 |
| 2004/0123343 A1 | 6/2004 | La Rosa et al. | |
| 2005/0272080 A1 | 12/2005 | Palma et al. | |
| 2010/0196356 A1 * | 8/2010 | Karlsson et al. | 424/130.1 |

FOREIGN PATENT DOCUMENTS

| | | |
|---|---|---|
| EP | 1 262 562 | 12/2002 |
| WO | WO 2004044123 A2 | 5/2004 |
| WO | WO 2004080148 A2 | 9/2004 |
| WO | WO 2007/004979 A1 | 1/2007 |
| WO | WO 2007019563 A2 | 2/2007 |
| WO | WO 2008136748 A1 | 11/2008 |

OTHER PUBLICATIONS

Database Genbank (Online) Accession No. AC134563, Jan. 24, 2006, retrieved from NCBI.

Kutsenko et al., "*Not*I Flanking Sequences: A Tool for Gene Discovery and Verification of the Human Genome," Nucleic Acids Res. (2002), 30(14):3163-3170, Oxford University Press.

Spiik A—K EL al. "Abrogated lymphocyte infiltration and lowered CD14 in dextran sulfate induced colitis in mice treated with p65 antisense oligonucleotides", International Journal of Colorectal Disease, 17(4): 223-232 (2002).

D'Acquisto F et al., "Local administration of transcription factor decoy oligonucleotides to nuclear factor-kappaB prevents carrageenin-induced inflammation in rat hind paw", Gene Therapy., 7(20):1731-1737 (Oct. 2000).

Database EMBL [Online] "Rabbit hemorrhagic disease virus isolate CD/China, complete genome", retrieved from EBI accession No. EMBL: AY523410; Database accession No. AY523410; (Feb. 9, 2004).

Database EMBL [Online] "Sequence 434292 from US 7374927", retrieved from EBI accession No. EMBL: GC234292; Database accession No. Gc234292, (Aug. 26, 2008).

* cited by examiner

*Primary Examiner* — Jane Zara
(74) *Attorney, Agent, or Firm* — Porter Wright Morris & Arthur LLP

(57) ABSTRACT

Isolated and substantially purified oligonucleotide compounds have been shown to be effective in reducing swelling and edema. Novel methods and substances are presented for the prevention, alleviation or treatment of edema of various aetiology.

28 Claims, 10 Drawing Sheets

SEQUENCE LISTING

<160> NUMBER OF SEQ ID NOS: 15

<210> SEQ ID NO 1
<211> LENGTH: 23
<212> TYPE: DNA
<213> ORGANISM: Artificial
<220> FEATURE:
<223> OTHER INFORMATION: Synthetic oligonucleotide

<400> SEQUENCE: 1
tgccattcgt cgttctcgtc gtt                                          23

```
<210> SEQ ID NO 2
<211> LENGTH: 23
<212> TYPE: DNA
<213> ORGANISM: Artificial
<220> FEATURE:
<223> OTHER INFORMATION: Synthetic oligonucleotide

<400> SEQUENCE: 2
tgccattcgt cgatttcgtc gat                                            23

<210> SEQ ID NO 3
<211> LENGTH: 21
<212> TYPE: DNA
<213> ORGANISM: Artificial
<220> FEATURE:
<223> OTHER INFORMATION: Synthetic oligonucleotide

<400> SEQUENCE: 3
tcgtcgttcg gccgatcgtc c                                              21

<210> SEQ ID NO 4
<211> LENGTH: 13
<212> TYPE: DNA
<213> ORGANISM: Artificial
<220> FEATURE:
<223> OTHER INFORMATION: Synthetic oligonucleotide

<400> SEQUENCE: 4
gggtcgtctg cgg                                                       13

<210> SEQ ID NO 5
<211> LENGTH: 17
<212> TYPE: DNA
<213> ORGANISM: Artificial
<220> FEATURE:
<223> OTHER INFORMATION: Synthetic oligonucleotide

<400> SEQUENCE: 5
tcccaagatc gtccagg                                                   17

<210> SEQ ID NO 6
<211> LENGTH: 14
<212> TYPE: DNA
<213> ORGANISM: Artificial
<220> FEATURE:
<223> OTHER INFORMATION: Synthetic oligonucleotide

<400> SEQUENCE: 6
tccgatcgtc cagg                                                      14

<210> SEQ ID NO 7
<211> LENGTH: 22
<212> TYPE: DNA
<213> ORGANISM: Artificial
<220> FEATURE:
<223> OTHER INFORMATION: Synthetic oligonucleotide

<400> SEQUENCE: 7
tcgtctgctt agttcgttag tt                                             22

<210> SEQ ID NO 8
<211> LENGTH: 24
<212> TYPE: DNA
<213> ORGANISM: Artificial
<220> FEATURE:
<223> OTHER INFORMATION: Synthetic oligonucleotide

<400> SEQUENCE: 8
```

-continued

```
tccgcgttcg gcctcctggc gcgg                                              24

<210> SEQ ID NO 9
<211> LENGTH: 15
<212> TYPE: DNA
<213> ORGANISM: Artificial
<220> FEATURE:
<223> OTHER INFORMATION: Synthetic oligonucleotide

<400> SEQUENCE: 9
ggggcgtctg ccggg                                                        15

<210> SEQ ID NO 10
<211> LENGTH: 22
<212> TYPE: DNA
<213> ORGANISM: Artificial
<220> FEATURE:
<223> OTHER INFORMATION: Synthetic oligonucleotide

<400> SEQUENCE: 10
tccatggtca gggtcccggg gg                                                22

<210> SEQ ID NO 11
<211> LENGTH: 19
<212> TYPE: DNA
<213> ORGANISM: Artificial
<220> FEATURE:
<223> OTHER INFORMATION: Positive control, KAPPAPROCT (R)

<400> SEQUENCE: 11
ggaacagttc gtccatggc                                                    19

<210> SEQ ID NO 12
<211> LENGTH: 19
<212> TYPE: DNA
<213> ORGANISM: Artificial
<220> FEATURE:
<223> OTHER INFORMATION: Synthetic oligonucleotide

<400> SEQUENCE: 12
ggaacagttc gtccatggc                                                    19

<210> SEQ ID NO 13
<211> LENGTH: 19
<212> TYPE: DNA
<213> ORGANISM: Artificial
<220> FEATURE:
<223> OTHER INFORMATION: Synthetic oligonucleotide

<400> SEQUENCE: 13
ggaacagttg ctccatggc                                                    19

<210> SEQ ID NO 14
<211> LENGTH: 20
<212> TYPE: DNA
<213> ORGANISM: Artificial
<220> FEATURE:
<223> OTHER INFORMATION: Fully phosphorothiolated mouse CpG-sequence
<300> PUBLICATION INFORMATION:
<301> AUTHORS: Kline JN
<302> TITLE: Modulation of airway inflammation by CpG
       oligodeoxynucleotides in a murine model of asthma
<303> JOURNAL: Journal of Immunology
<304> VOLUME: 1998
<305> ISSUE: 160
<306> PAGES: 2555-2559
<307> DATE: 1998-03-15
```

```
<400> SEQUENCE: 14
tccatgacgt tcctgacgtt                                              20

<210> SEQ ID NO 15
<211> LENGTH: 21
<212> TYPE: DNA
<213> ORGANISM: Artificial
<220> FEATURE:
<223> OTHER INFORMATION: Synthetic oligonucleotide

<400> SEQUENCE: 15
ggggaacagt tcgtccatgg c                                            21
```

COMPOUNDS FOR THE TREATMENT OR ALLEVIATION OF EDEMA, AND METHODS FOR THEIR USE

CROSS REFERENCE TO RELATED APPLICATIONS

Figure 1:
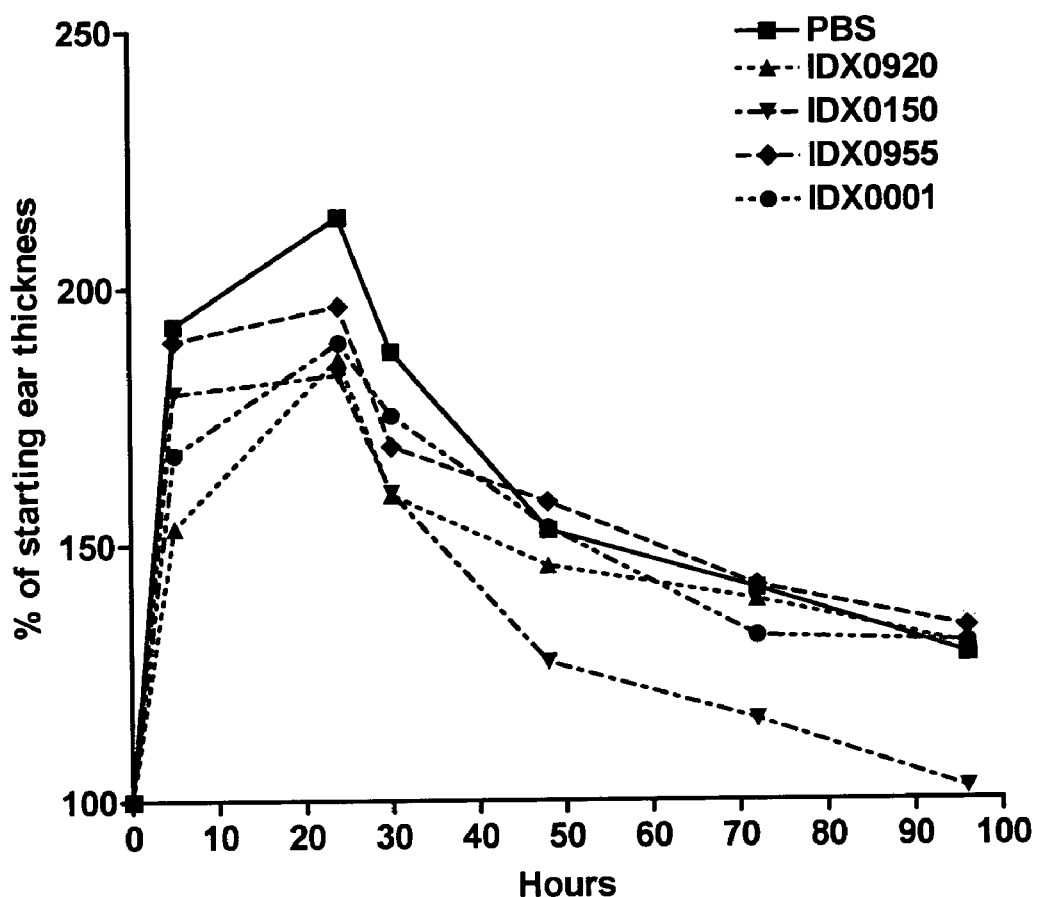

This application is a 35 USC §371 National Stage application of International Application No. PCT/SE2008/000542 filed Oct. 2, 2008, now pending; which claims the benefit under 35 USC §119(e) to U.S. Application Ser. No. 60/978,010 filed Oct. 5, 2007, now expired. The disclosure of each of the prior applications is considered part of and is incorporated by reference in the disclosure of this application.

TECHNICAL FIELD

This invention and embodiments thereof relates to the field of medicine, and in particular to novel compounds and methods for use in the treatment or alleviation of edema, a disorder or dysfunction in the interstitial fluid balance in any organ or tissue, encountered in several medical conditions.

BACKGROUND

Edema can be defined as an abnormal accumulation of fluid in the interstices of cells in tissue spaces or in body cavities. It can be caused either by excessive movement of fluid from the vascular system into the tissues or inadequate movement of fluid from the tissues back to the vascular system. The normal interchange of fluid between these two compartments is regulated by the 'Starling equation' of tissue fluid, whereby the generation of interstitial fluid depends on the balance of osmotic pressure and hydrostatic pressure acting in opposite directions across the semi-permeable capillary walls. Edema is the result of an imbalance in these forces, which tends to cause abnormal accumulation of fluid in the interstitial spaces.

Clinical manifestations of edema include mild to severe swelling of the body and a gain in body weight. The swelling can be caused either by a generalised (or systemic) increase in extra cellular fluid or due to edematous collections that confined to a localised site. Anasarca, the medical condition for generalised edema, is marked by the swelling of the subcutaneous tissues, while localised edema is normally designated, based on the affected site, such as hydrothorax (excess serous fluid in the spaces between the pleura), hydropericardium (excess fluid in the pericardial sac), hydroperitoneum or ascites (excess fluid in the peritoneal cavity), amongst others.

The composition of the extravascular fluid that accumulates in edema varies according to its etiology. In the case of edema caused by non-inflammatory mechanisms, the fluid (transudate) comprises a relatively low protein concentration and is of less specific gravity, indicating that the endothelium of the affected site is normal. In such cases, the transudate is essentially an ultrafilterate of blood plasma. This kind of non-inflammatory edema is primarily caused by alterations in the hemodynamic forces across the capillary wall and is also known as hemodynamic edema. On the other hand, in the case of edema that is caused by an inflammatory response, the extravascular fluid (exudate) comprises a high concentration of protein, cells and cellular debris and has high specific gravity. This indicates a significant alteration in the normal permeability of the small blood vessels in the affected area.

Edema normally occurs as an important functional manifestation of the pathogenesis of various diseases, but can also occur as result of trauma and injury. Heart failure, cirrhosis of the liver and kidney diseases such as nephrotic syndrome are some of the most common systemic diseases that cause edema. The main mechanisms involved in the development of edema during disease pathogenesis include increased intravascular hydrostatic pressure, impairment in the flow of lymph, inappropriate renal sodium and water retention, reduced plasma osmotic pressure, and increased vascular permeability.

Increase in hydrostatic pressure in the veins results in poor re-absorption of fluids from the tissue, and this imbalance results in edema. The increase in hydrostatic pressure may either occur as a generalised increase in venous pressure or affect only a specific site. A local increase in the hydrostatic pressure may result from impaired venous outflow, which is usually encountered in the lower extremities and is secondary to the development of obstructive thrombosis and varicose veins. The resulting edema is localised in the legs and lower limbs, commonly known as peripheral edema. A generalised increase in venous pressure results in systemic edema, which is commonly observed in the case of congestive heart failure. Specifically, failure of the left side of the heart results in fluid collection in the lungs (alveoli), resulting in pulmonary edema and dyspnea. On the other hand, during failure of the right side of the heart, fluid accumulates in the lower limbs, causing peripheral edema. As the condition progresses or worsens, the upper limbs also swell, and eventually, there is collection of fluid in the peritoneal cavity, which results in an edematous condition known as ascites. It has been observed that causes of edema, which are generalised in the whole body, can cause edema in multiple organs.

Impaired flow of lymph or lymphatic obstruction results in inadequate drainage of interstitial fluid, which consequently causes localised lymphedema. Lymphedema is a common debilitating edematic condition in which excess lymph collects in tissues. It may be caused by an inflammatory or neoplastic obstruction, pressure from a cancer or an enlarged lymph node, destruction of lymph vessels by radiotherapy, or the infiltration of lymphatics by infections such as elephantiasis or filariasis, amongst others.

Excessive retention of sodium and water by the kidneys causes an increase in the volume of intravascular fluid, which eventually increases the hydrostatic pressure and causes edema. Conditions such as acute renal failure or streptococcal glomerulonephritis, amongst others, directly affect normal renal function and cause abnormal salt retention in the body. Apart from this, pathogenesis of several disorders such as congestive heart failure, hypoalbuminemia, etc., activates the renin-angiotensin-aldosterone (RAAS) hormonal system, which promotes sodium and water retention. Hence, edema that is initiated by one mechanism gets complicated by the secondary mechanism of salt and fluid retention. An extra fluid load in the body and the vicious circle of fluid retention further imbalances the pressure gradient across the membranes and results in worsening of the edema.

Decreased plasma osmotic pressure inside the vessels facilitates the movement of fluids towards the interstitial spaces, resulting in edema. Such a decrease in plasma osmotic pressure can be the result of either an excessive loss or reduced synthesis of plasma proteins that are impermeable to the capillary membrane, especially albumins, which primarily contribute to maintain the blood volume. The most important cause of excessive loss of albumin is a kidney disorder known as the nephrotic syndrome, which is characterised by a leaky glomerular basement membrane, and which eventually results in generalised edema. Reduced synthesis of serum proteins, especially albumins (or hypoalbuminemia), occurs in diffuse diseases of the liver, such as cirrhosis, or is associated with malnutrition. In all these instances, the movement of fluid from the intravascular to the interstitial compartment results in a contraction in the volume of plasma, which results in generalised edema-like symptoms such as ascites and peripheral edema, amongst others.

Another important cause for excessive loss of plasma proteins is an increase in the permeability of blood vessels to plasma proteins. This increased permeability causes movement of proteins and cells, such as leukocytes from the circulation to the interstitium. The loss of protein-rich fluid from the plasma reduces the intravascular osmotic pressure and increases the osmotic pressure of the interstitial space, which eventually results in an outflow of fluid from the blood vessels to the interstitium, causing edema. An increase in vascular permeability is one of the main characteristics of the inflammatory response of the body against stimuli, especially in the case of acute inflammation. In fact, edema is one of the main signs of acute inflammation. During inflammation, the chemical factors derived from plasma and triggered by inflammatory stimuli mediate a number of vascular and cellular responses in the affected site. These structural changes in the microvasculature result in increased permeability of the blood vessel membrane, causing movement of plasma proteins and cells, e.g. leukocytes from the circulation to the intersititium, which ultimately results in site-specific edema. Inflammatory edema can be largely attributed to the direct action of histamine, bradykinin and other the substances released. The main mechanisms of increased vascular permeability in inflammation include endothelial cell contraction, junctional retraction, direct injury, leukocyte-dependent leakage, regenerating endothelium, amongst others. Increased fluid filtration towards the interstitium is further enhanced by the arteriolar vasodilator action of the inflammatory mediators, which increases the blood flow, the perfused surface area, capillary hydrostatic pressure, and facilitates edema by other mechanisms as well.

In summary, edema is known as one of the important functional manifestations of the pathogenesis of various diseases. Heart failure, cirrhosis of the liver, nephrotic syndrome, amongst others, are some of the most common systemic diseases that eventually result in edema. Understanding the dynamics of edema and the other related clinical manifestations associated with these diseases is important for deciphering their complete pathology and may also help in developing novel and highly specific diagnostic, therapeutic and preventive strategies towards these diseases.

One objective is to make available novel compounds and methods for the prevention, alleviation or treatment of edema. Other objectives and their associated advantages will become apparent upon study of the description and examples.

SUMMARY

The inventors make available novel compounds and methods for the prevention, treatment or alleviation of edema as set out in the attached claims, incorporated herein by reference. The present inventors surprisingly found that an oligonucleotide compound comprising a sequence selected from the group comprising SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, and SEQ ID NO 10, is effective in the treatment or alleviation of edema.

According to one embodiment of the invention, the oligonucleotide compounds, comprising at least one of the sequences SEQ ID NO 1-10, have a total length between about 12 and about 30 bases.

The inventors have identified and tested individual oligonucleotide sequences, and shown their usefulness in the treatment or alleviation of edema.

Based on these findings, the inventors present specific compounds as disclosed in the attached claims. These compounds have been tested both in vitro and in vivo, and the experimental results tentatively support the theory that the compounds reduce edema by reducing vascular permeability.

SHORT DESCRIPTION OF THE FIGURES

The embodiments will be described in closer detail below, in the description, examples and claims, which are to be studied together with the attached drawings in which:

FIG. 1 is a graph showing the anti-inflammatory effect of test- and control drugs in a tetradecanoylphorbol 13-acetate (TPA) induced ear edema model. IDX0920 (50 µg), IDX0150 (100 µg), IDX0955 (100 µg) and the test drug IDX0001 (100 µg) given as one single s.c. injection 20 minutes before administration of TPA. Initial thickness of the ears set as 100%. Reduction of area under the curve (AUC) compared to PBS is for IDX0920 −22.1% (P<0.011), IDX0150 −38.9% (P<0.011), IDX0955 −4.8% and IDX0001 −15.7% (P>0.05). One-way ANOVA with Dunnett's Multiple Comparison Test.

Figure 2:
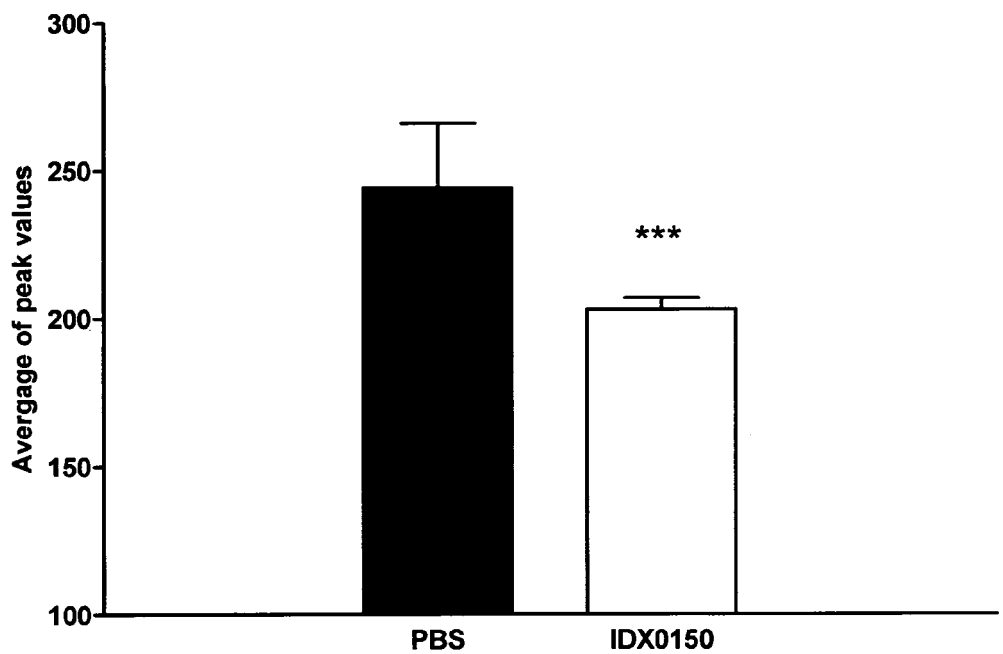

FIG. 2 Results from the TPA-induced ear edema model showing the average inflammatory peak value of swelling after administration of 100 µg IDX0150 combined from 10 experiments with the TPA model in comparison to negative control (PBS vehicle with TPA). Students t-test, ***P<0.001, ±SD.

Figure 3A:
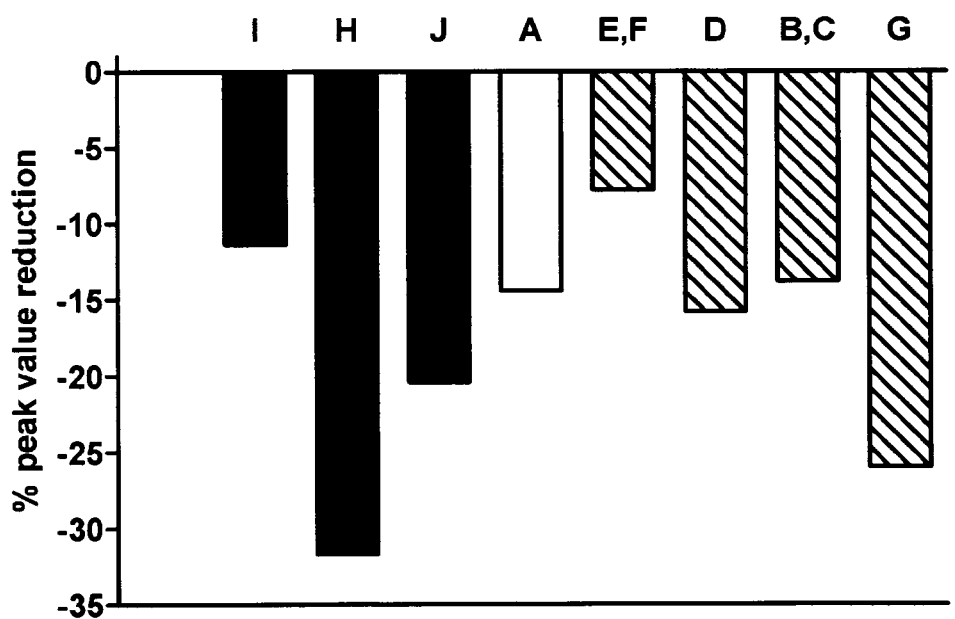

FIG. 3a is a combined histogram from the TPA-induced ear edema model. Edema peak value reduction by IDX0150 treatment, compared to vehicle (PBS) treatment. Black bars, intranasal (i.n.), open bar, intraperitoneal (i.p.) and hatched bars, subcutaneous (s.c.) administrations.

Treatment with IDX0150 at: −4 days before TPA administration (I, E and F), −2 days before TPA administration (D), −20 min before TPA administration (H, A, B and C), +2 h after TPA administration (J and G). In all cases 100 µg IDX0150/mouse was used for the treatment, except for study F where 50 µg IDX0150/mouse was used. E,F or B,C are mean of two experiments.

Figure 3B:
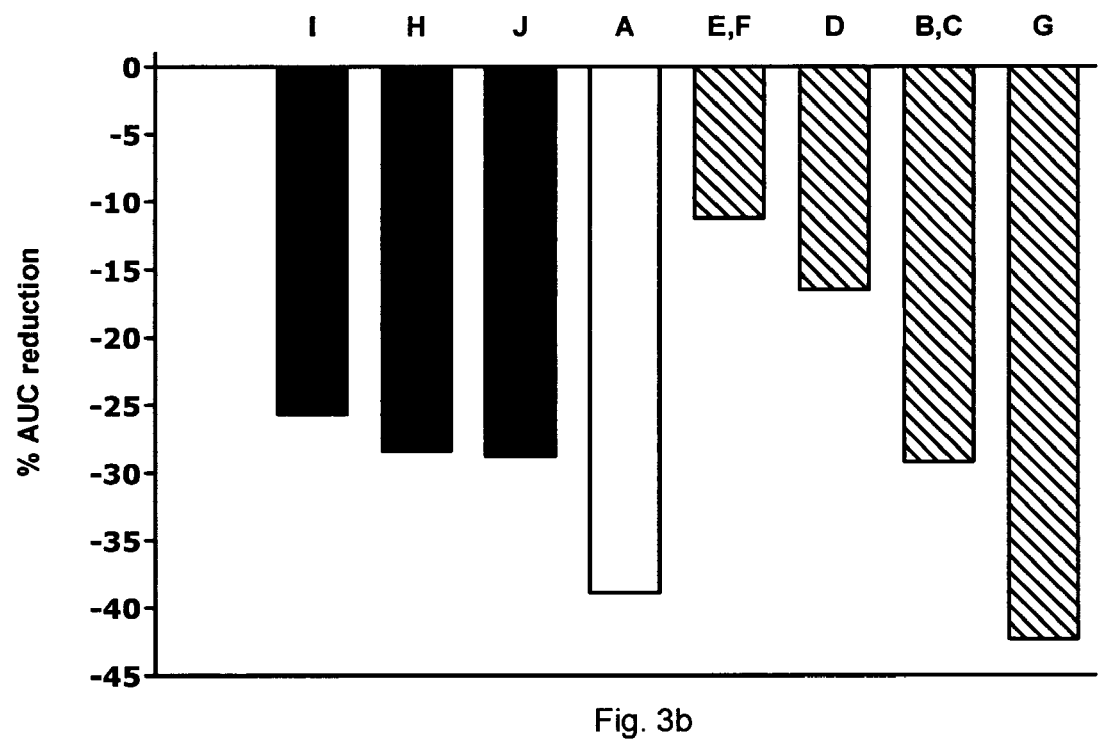

FIG. 3b is a combined histogram from the TPA-induced ear edema model. Edema area under the curve (AUC) reduction by IDX0150 treatment, compared to vehicle (PBS) treatment. Black bars, intranasal (i.n.), open bar, intraperitoneal (i.p.) and hatched bars, subcutaneous (s.c.) administration. Treatment with IDX0150 at: −4 days before TPA administration (I, E and F), −2 days before TPA administration (D), −20 min before TPA administration (H, A, B and C), +2 h after TPA administration (J and G). In all cases 100 µg IDX0150/mouse was used for the treatment, except for study F where 50 µg IDX0150/mouse was used. E,F or B,C are mean of two experiments.

Figure 4:
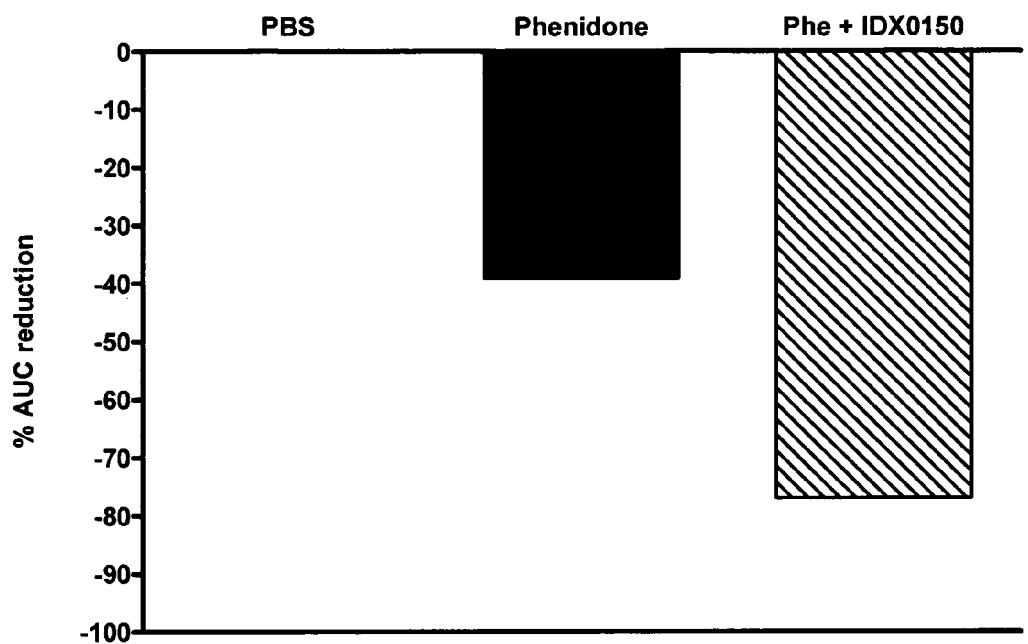

FIG. 4 is a histogram showing the effect of phenidone and IDX0150 in the arachidonic acid (AA) induced ear edema model. Phenidone, given 30 min before AA induction showed reduction of AUC −39.1%, P<0.05, which was similar to treatment with IDX0150 obtained earlier (see FIG. 2). Phenidone given 30 min before AA, combined with IDX0150 given 20 min before AA, resulted in a further reduction (−76.8%, P<0.001).

Figure 5A:
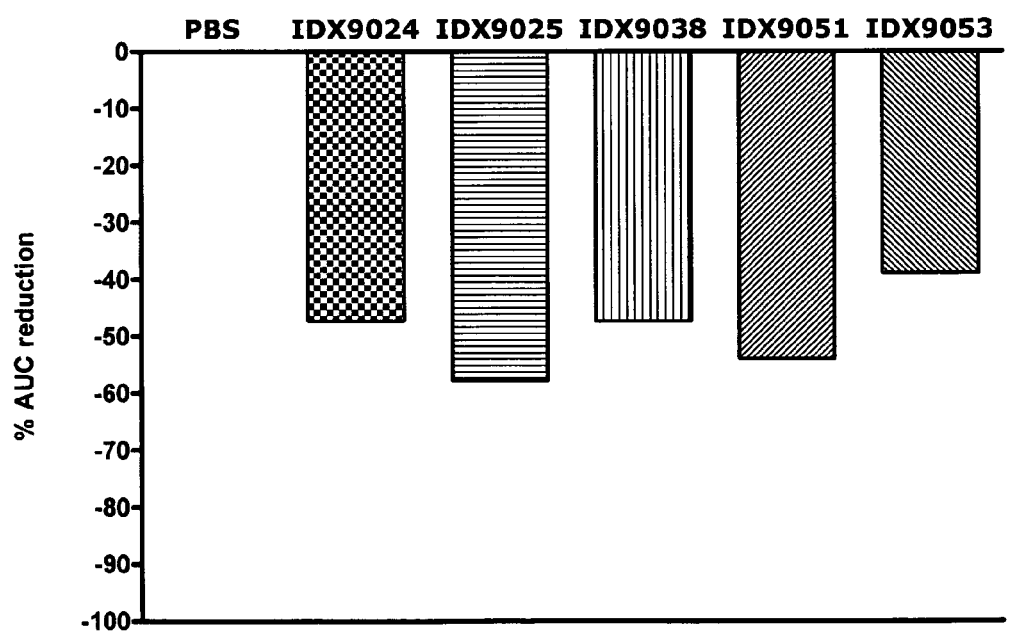

FIG. 5a is a graph showing the anti-inflammatory effect of test drugs and vehicle (PBS) in a TPA-induced ear edema model. Ten µg of IDX9024, IDX9025, IDX9038, IDX9051 and IDX9053 was given as one single s.c. injection 20 minutes before administration of TPA. Initial thickness of the ears set as 100%. AUC reduction for IDX9024 −47.3%, IDX9025 −57.8%, IDX9038 −47.4%, IDX9051 −54.0% and IDX9053 −39.0% compared to PBS control.

Figure 5B:
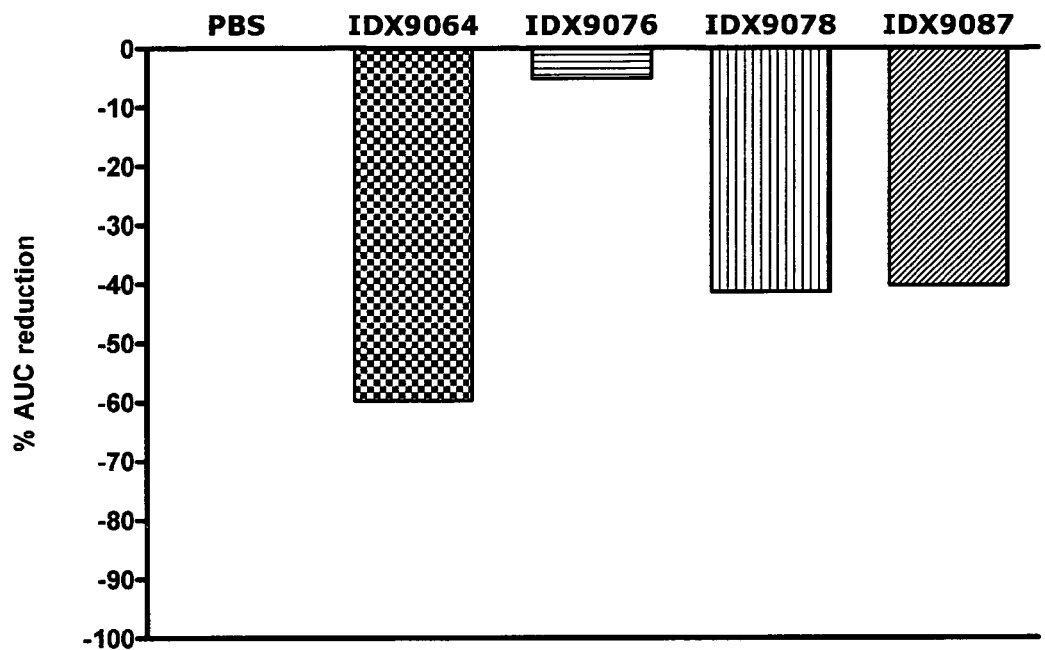

FIG. 5b is a graph showing the anti-inflammatory effect of test drugs and vehicle (PBS) in a TPA-induced ear edema model. Ten µg of IDX9064, IDX9076, IDX9078, IDX9080 and IDX9089 was given as one single s.c. injection 20 minutes before administration of TPA. Initial thickness of the ears set as 100%. AUC reduction for IDX9064 −59.7%, IDX9076 −5.1%, IDX9078 −41.3%, IDX9087 −40.2% compared to PBS control.

Figure 5C:
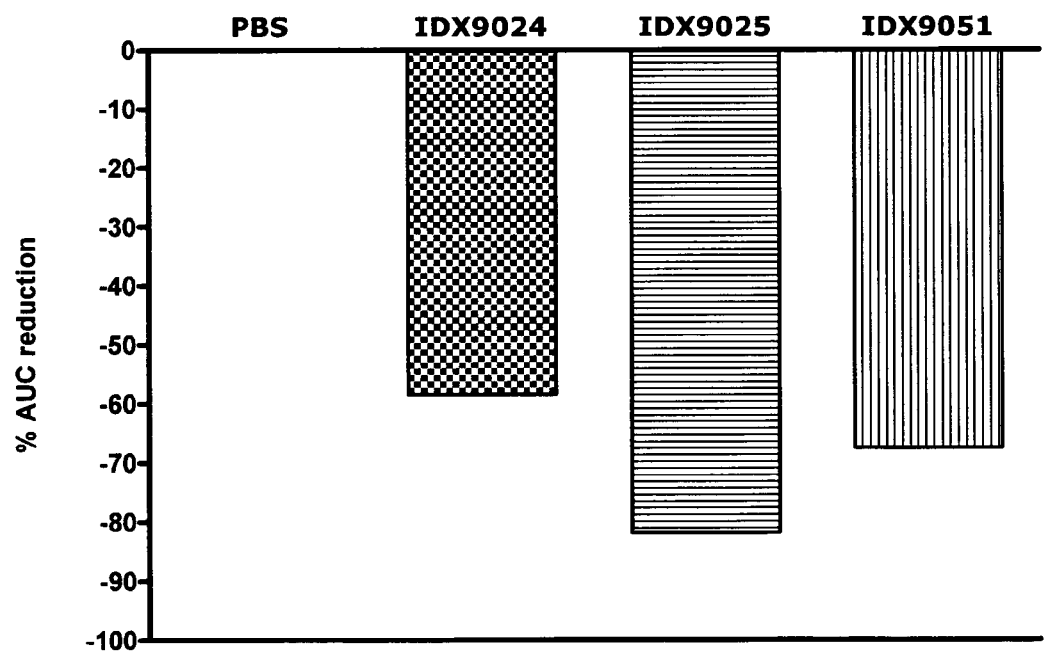

FIG. 5c is a graph showing the anti-inflammatory effect of test drugs and vehicle (PBS) in an AA-induced ear edema model. Ten µg of IDX9024, IDX9025 and IDX9051 was given as one single s.c. injection 20 minutes before administration of AA. Initial thickness of the ears set as 100%. AUC reduction for IDX9024 −58.5%, IDX9025 −81.9% and IDX9051 −67.5% compared to PBS control.

Figure 5D:
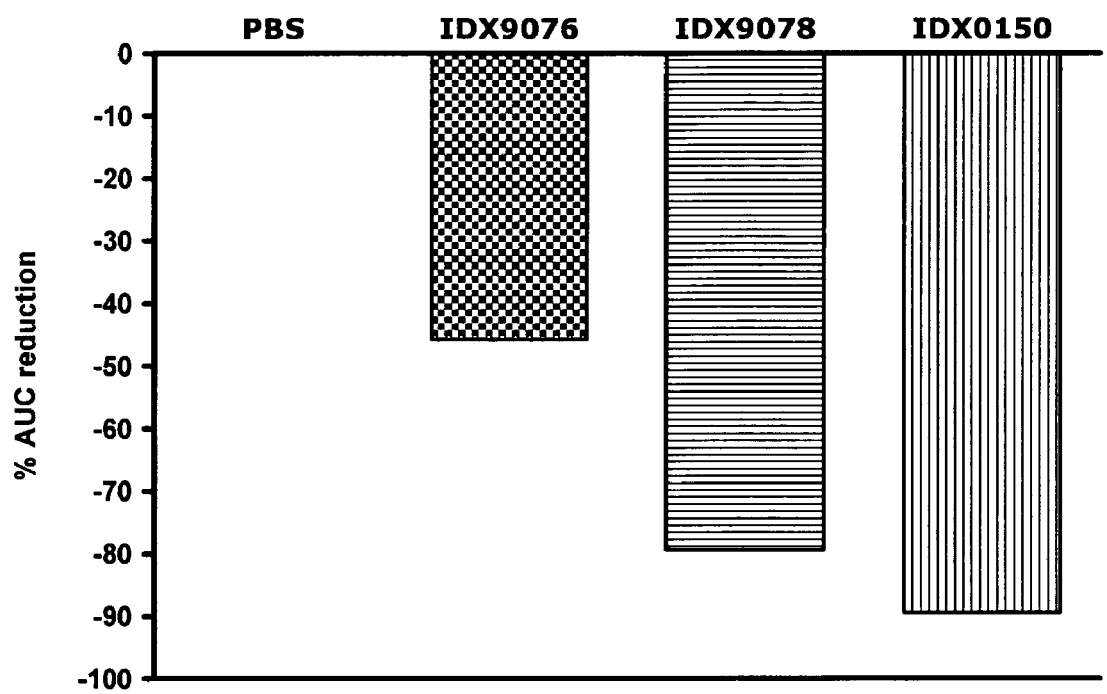

FIG. 5d is a graph showing the anti-inflammatory effect of test drugs and vehicle (PBS) in an AA-induced ear edema model. Ten µg of IDX9076, IDX9078 and IDX0150 was given as one single s.c. injection 20 minutes before administration of AA. Initial thickness of the ears set as 100%. AUC reduction for IDX9076 −45.7%, IDX9078 −79.4% and IDX0150 −89.4% compared to PBS control.

Figure 6:
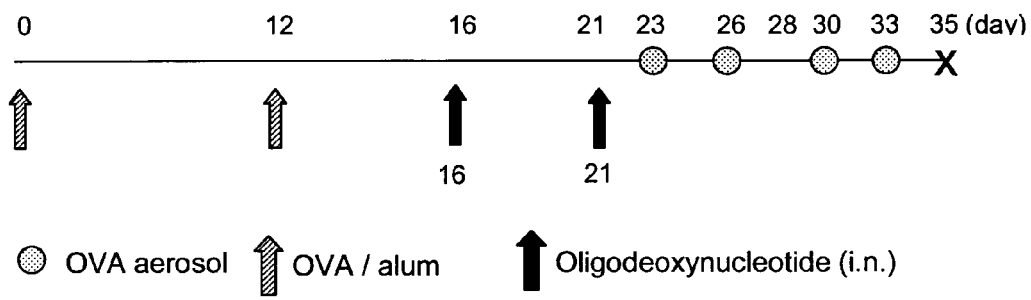
Figure 6:
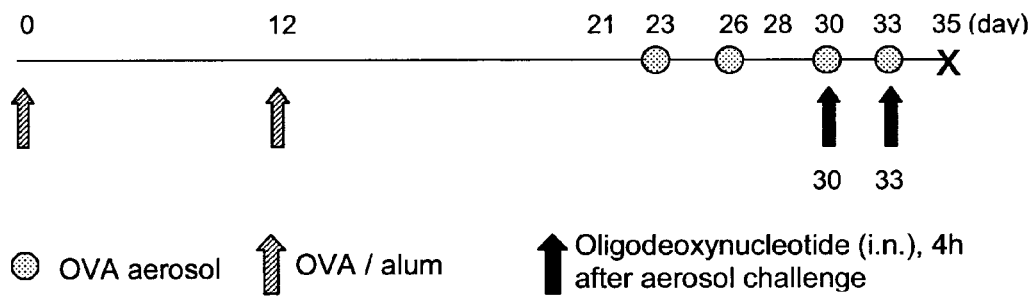
Figure 6:
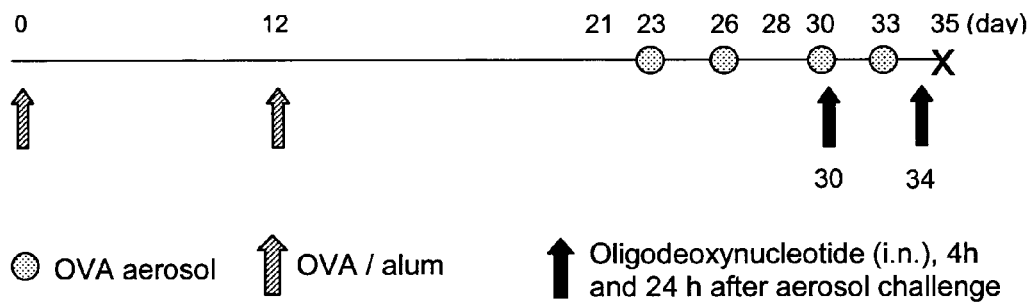

FIG. 6 shows the prophylactic and therapeutic protocols for the murine model of ovalbumin (OVA) induced allergic airway inflammation.

Figure 7:
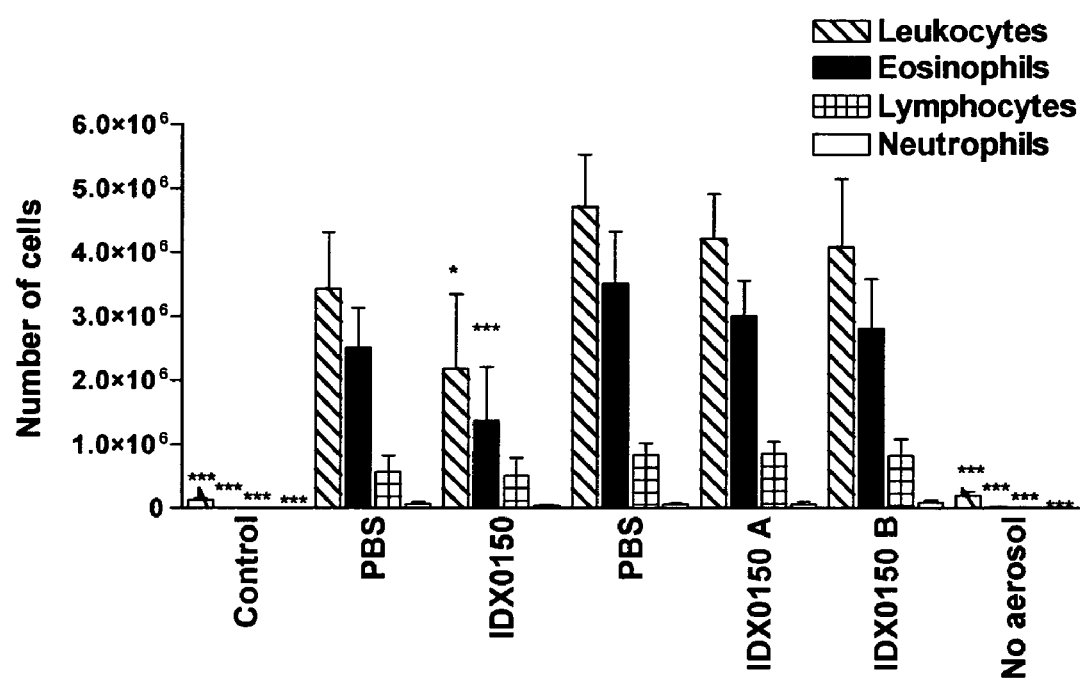

FIG. 7 is a combined histogram showing the total number of different cell types in bronchial alveolar lavage (BAL) fluid from OVA immunised Balb/c mice, 48 h after the last OVA aerosol. Mice were treated with IDX0150 (50 µg/animal) administered by intranasal instillation on day 16 and 21 in a prophylactic protocol (IDX0150, see M&M). In a therapeutic protocol IDX0150 was given on day 30 and 33 (IDX0150 A, see M&M), or on day 30 and 34 (IDX0150 B). The instillations in the therapeutic protocols (A & B) on day 30 and 33 were given 4 h after aerosol challenge. The second instillation in protocol B, on day 34, was given 24 h after the last aerosol challenge. Healthy controls were treated with PBS and exposed to OVA aerosol. Data shown as mean±SD. * $P<0.05$, *** $P<0.001$ using One-way analysis of variance (ANOVA), Dunnett's post hoc correction. The PBS group was sham-treated with PBS and exposed to OVA aerosol.

Figure 8:
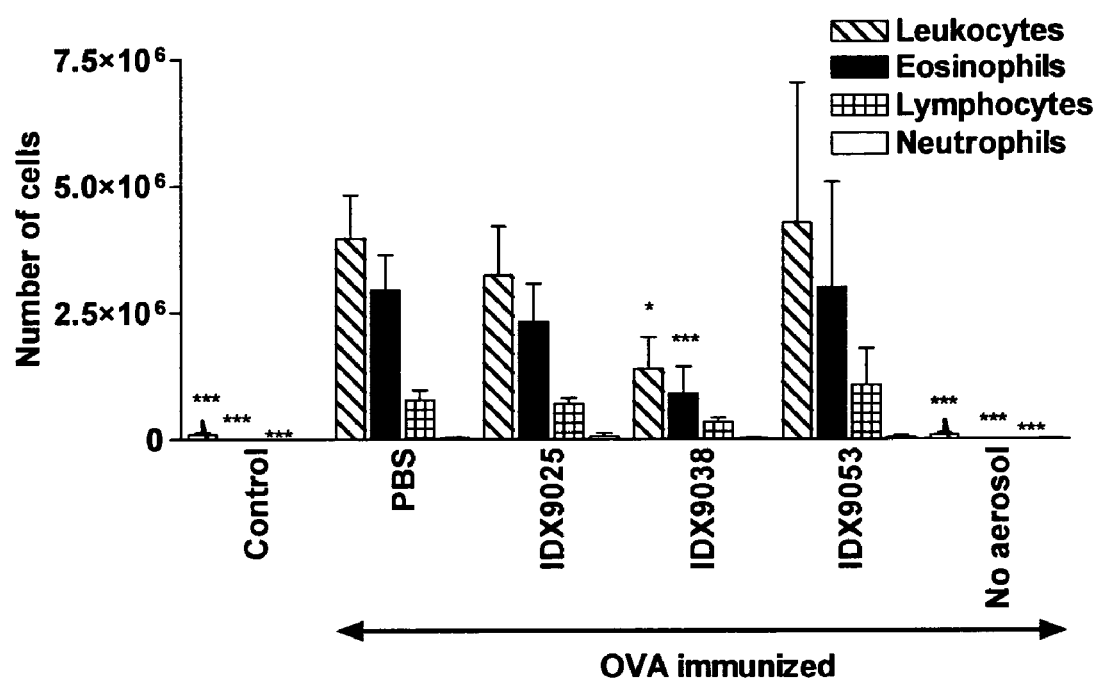

FIG. 8 is a combined histogram showing the results of a prophylactic protocol in the OVA induced allergic asthma model. Total number of cells in bronchial alveolar lavage (BAL) fluid from OVA immunized Balb/c mice, 48 h after the last OVA aerosol (first day 0 and last on day 12). Mice were treated with IDX9025, IDX9038 or IDX9053 (50 µg/animal) administered by intranasal instillation on day 16 and 21 after first immunization. The PBS group was immunized and sham-treated with PBS and exposed to OVA aerosol. Data shown as mean±SD. * $P<0.05$, *** $P<0.001$ using One-way analysis of variance (ANOVA), Dunnett's post hoc correction.

Figure 9A:
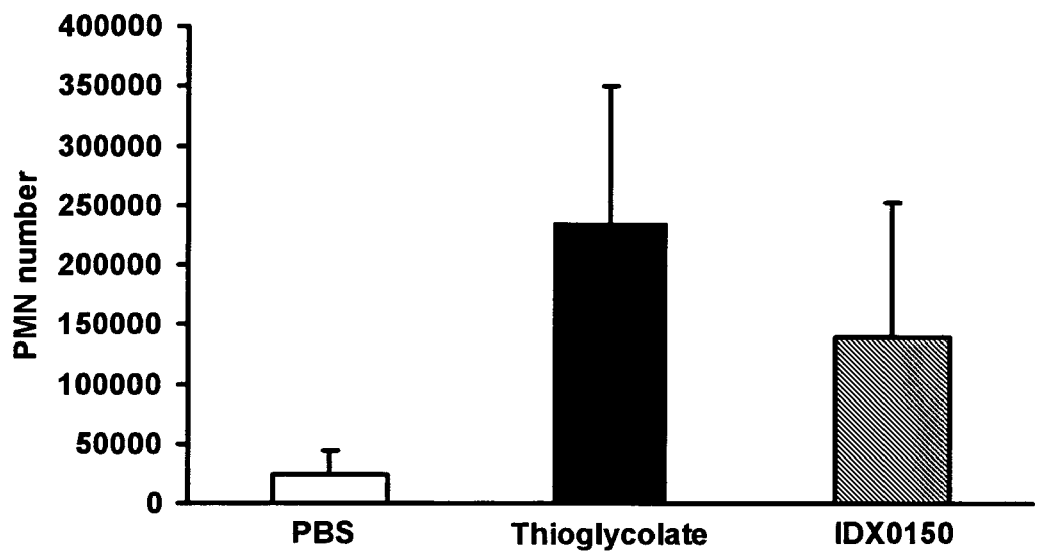

FIG. 9a is a histogram showing the result of intraperitoneal treatment with 50 µg IDX0150/mouse, given 20 min before induction of thioglycolate induced pleurisy. The number of polymorphonuclear cells (PMN's) in pleural exudates showed a 40.9% reduction after IDX0150 treatment compared to inflamed mice (PBS). Data shown as mean±SD.

Figure 9B:
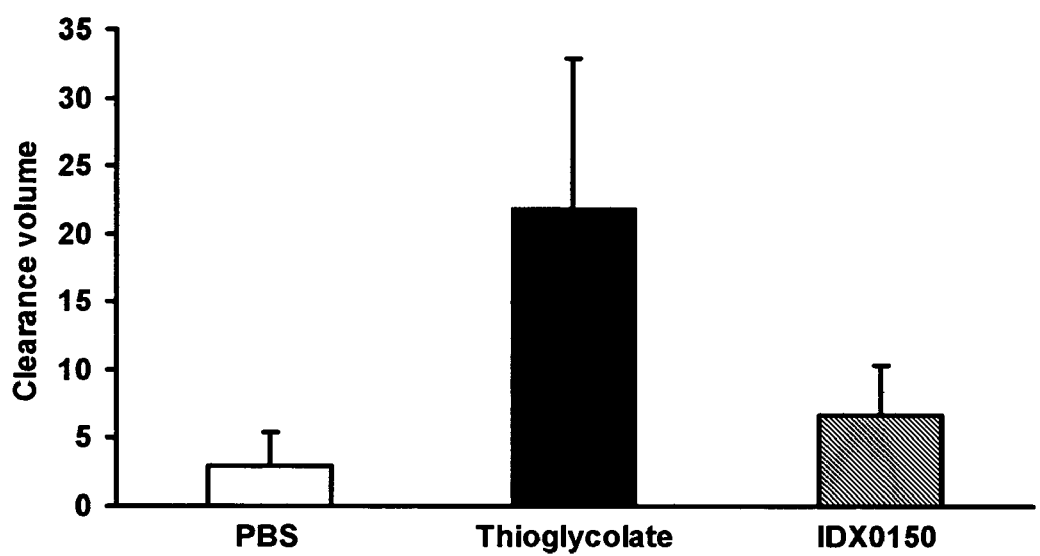

FIG. 9b is a histogram showing the result of intraperitoneal treatment with 50 µg IDX0150/mouse, given 20 min before induction of thioglycolate induced pleurisy. The IDX0150 showed a reduction in clearance volume of pleural edema with 69.2% compared to thioglycolate treatment. Data shown as mean±SD.

DETAILED DESCRIPTION

Before the embodiments are described, it is to be understood that the terminology employed herein is used for the purpose of describing particular embodiments only and is not intended to be limiting, since the scope of the embodiments will be limited only by the appended claims and equivalents thereof.

It must be noted that, as used in the present description and in the appended claims, the singular forms "a", "an", and "the" include plural referents unless the context clearly dictates otherwise.

The terms "alleviation", "treatment", "prevention", "therapy", "therapeutic use", "prophylactic use", "medicament", and "medical use" when used in the description and claims encompass both human and animal or veterinary applications. Importantly, the term "treatment" is here used in its broadest sense, not limited to reversing or curing a disease, but also including the alleviation of the symptoms or the retardation of the progression of the disease.

Further, when using the term "method of treatment" also method steps and adjunct methods are encompassed, i.e. cases where the disclosed methods as such do not constitute the exhaustive method. It is contemplated that the inventive methods may constitute a step in a series of actions and measures, leading to the alleviation, prevention or treatment of a disease.

The term "about" when used in the context of numeric values denotes an interval of accuracy, familiar and acceptable to a person skilled in the relevant art. Said interval can be +/−10% or preferably +/−5%.

The phrase "therapeutically effective amount" as used herein relates to an amount sufficient to inhibit or reduce edema to some beneficial degree, preferably to by at least about 10%, more preferably by at least 20%, and even more preferable by at least 30% or more, measured as reduction of peak value, or other relevant measure.

As used herein, the term "physiologically acceptable" refers to a material that is compatible with a biological system such as a cell, cell culture, tissue, or organism. Preferably, the biological system is a living organism, such as a vertebrate.

As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. Examples of carriers particularly suitable for mucosal administration include, but are not limited to saline, liposomes, surfactants, mucoadhesive compounds, enzyme inhibitors, bile salts, absorption enhancers, and cyclodextrins. The preparation of pharmaceutically acceptable formulations containing these materials are described in, e.g., Remington's Pharmaceutical Sciences, 18th Edition, ed. A. Gennaro, Mack Publishing Co., Easton, Pa., 1990.

For purposes of this description, the term "immunomodulatory" refers to the properties of a compound, e.g. an oligonucleotide as defined in the present description and claims, to induce an immune response either stimulating the immune system or repressing the immune system or both in an organism when administered to a vertebrate, such as a mammal. As used herein, the term "mammal" includes, without limitation rats, mice, cats, dogs, horses, cattle, cows, pigs, rabbits, non-human primates, and humans.

For purposes of this description, the term "oligonucleotide" refers to a polynucleoside formed from a plurality of linked individual nucleoside units. Such oligonucleotides can be obtained from existing nucleic acid sources, including genomic or cDNA, but are preferably produced by synthetic methods. The nucleoside residues can be coupled to each other by any of the numerous known internucleoside linkages. Such internucleoside linkages include, without limitation, the natural internucleoside phosphodiester bond or indeed modified internucleosides such as, but not limited to, phosphorodithioate, phosphorothioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., (Rp)- or (Sp)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, or phosphorodithioate linkages, or combinations thereof.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers.

The term "mucosal administration" includes administration to any of the types of mucosa in the animal body, for example, but not limited to nasal, buccal, oesophagal, astric, intestinal, olfactory, oral, bronchial and urogenital mucosa.

The different embodiments make available isolated and substantially purified oligonucleotide compounds comprising a sequence chosen among the sequences SEQ ID NO 1-10. Specific sequences are presented in Tables 1 and 2 below. It is noted that the sequences of Table 1, SEQ ID NO 1-7 share the following sequence or motif: 5'-TCGTC-3'

It is envisaged that compounds according to various embodiments of the invention, comprising the sequences, preferably have a total length between about 12 and about 30 bases.

TABLE 1

Examples of oligonucleotide sequences
Table 1

| SEQ ID NO | IDX-No | Seq 5'-3' |
|---|---|---|
| 1 | IDX9024 | T*G*C*CATTCGTCGTTCTCGTC*G*T*T |
| 2 | IDX9025 | T*G*C*CATTCGTCGATTTCGTC*G*A*T |
| 3 | IDX9038 | T*C*G*TCGTTCGGCCGATCG*T*C*C |
| 4 | IDX9053 | G*G*G*TCGTCTG*C*G*G |

TABLE 1-continued

Examples of oligonucleotide sequences
Table 1

| SEQ ID NO | IDX-No | Seq 5'-3' |
|---|---|---|
| 5 | IDX9076 | T*C*C*CAAGATCGTCC*A*G*G |
| 6 | IDX9078 | T*C*C*GATCGTCC*A*G*G |
| 7 | IDX9087 | T*C*G*TCTGCTTAGTTCGTTA*G*T*T |

*= phosphorothioate modification

TABLE 2

Examples of oligonucleotide sequences
Table 2

| SEQ ID NO | IDXs-No | Seq 5'-3' |
|---|---|---|
| 8 | IDX0001 | T*C*C*GCGTTCGGCCTCCTGGCG*C*G*G |
| 9 | IDX9051 | G*G*G*GCGTCTGCC*G*G*G |
| 10 | IDX9064 | T*C*C*ATGGTCAGGGTCCCGG*G*G*G |

*= phosphorothioate modification

The inventors also used different oligonucleotide sequences as positive and negative controls. These are listed in Table 3.

TABLE 3

Examples of oligonucleotides used as controls
Table 3

| SEQ ID NO | IDXs-No | Seq 5'-3' |
|---|---|---|
| 11 | IDX0150 | G*G*A*ACAGTTCGTCCAT*G*G*C |
| 12 | IDX0500 | G*G*A*A*C*A*G*T*T*C*G*T*C*C*A*T*G*G*C |
| 13 | IDX0526 | G*G*A*ACAGTTGCTCCAT*G*G*C |
| 14 | IDX0920 | T*C*C*A*T*G*A*C*G*T*T*C*C*T*G*A*C*G*T*T |
| 15 | IDX0955 | G*G*G*GAACAGTTCGTCCAT*G*G*C |

*= phosphorothioate modification

According to an embodiment of the invention, the oligonucleotide according to the general formula 1, an oligonucleotide chosen among SEQ ID NO 1-7, or an oligonucleotide chosen among SEQ ID NO 8-10, can be chemically modified. This chemical modification is for example a phosphate backbone modification of at least one nucleotide. Preferably, the phosphate backbone modification is a phosphorothioate or phosphorodithioate modification.

Other embodiments make available pharmaceutical compositions comprising an oligonucleotide chosen among SEQ ID NO 1-7, or an oligonucleotide chosen among SEQ ID NO 8-10. Such pharmaceutical compositions further preferably comprise a pharmacologically compatible and physiologically acceptable excipient or carrier.

According to one embodiment of the invention, a pharmaceutical composition comprising an oligonucleotide as defined above further comprises a pharmacologically compatible and physiologically acceptable excipient or carrier chosen from saline, liposomes, surfactants, mucoadhesive compounds, enzyme inhibitors, bile salts, absorption enhancers, cyclodextrins, etc. A skilled person will readily choose the necessary excipient or carrier without an inventive effort.

A currently preferred embodiment concerns a pharmaceutical formulation for mucosal administration, comprising an oligonucleotide chosen among SEQ ID NO 1-7, or an oligonucleotide chosen among SEQ ID NO 8-10. The embodiments of the invention also concerns the use an oligonucleotide chosen among SEQ ID NO 1-7, or an oligonucleotide chosen among SEQ ID NO 8-10, for the manufacture of a pharmaceutical composition for the prevention, treatment, and/or alleviation of edema.

This use according to one embodiment of the invention, is preferably focused to the prevention, treatment, and/or alleviation of a condition or disorder involving edema, where edema is defined as a disorder or dysfunction in interstitial fluid balance in any organ or tissue, linked to a condition chosen among for example heart failure, liver cirrhosis, kidney diseases such as nephrotic syndrome, malnutrition, cancer, asthma, allergic rhinitis, chronic obstructive pulmonary disease (COPD), ischemia, trauma and septic shock.

In such use according to embodiments of the invention, said oligonucleotide is administered in a physiologically acceptable and therapeutically effective amount, i.e. an amount effective to achieve one of regulate of vascular permeability, inhibition or reduction of leukocyte migration, inhibition or reduction of neutrophil migration or activation, inhibition or reduction of eosinophil migration, and inhibition or reduction of lymphocyte migration.

According to one embodiment of the invention, the oligonucleotide is chosen from the group consisting of SEQ ID NO 1-7, or an oligonucleotide chosen among SEQ ID NO 8-10, and used for treating asthma by inhibition or reduction of neutrophil migration or activation.

The embodiments of the invention also make available methods for the prevention, treatment, and/or alleviation of edema, wherein an oligonucleotide chosen among SEQ ID NO 1-7, or an oligonucleotide chosen among SEQ ID NO 8-10, is administered in a dose effective to achieve one or several of modification of vascular permeability, inhibition of neutrophil migration and/or activation, inhibition or reduction of eosinophil migration, inhibition or reduction of leukocyte migration, and inhibition or reduction of lymphocyte migration.

In general terms, the embodiments of the invention make available methods for the prevention, treatment, and/or alleviation of edema, wherein a pharmaceutical composition comprising an oligonucleotide chosen among SEQ ID NO 1-7, or an oligonucleotide chosen among SEQ ID NO 8-10, is administered to a patient. Suitable routes of administration are chosen from mucosal administration, transdermal, subcutaneous administration, and intraperitoneal administration.

According to one embodiment, the mucosal administration is chosen from gastric, nasal administration, inhalation, ocular administration, rectal administration, urogenital and vaginal administration.

Based on the significant anti-swelling and anti-edema effects recorded in the animal experiments conducted by the inventors, the methods of prevention, treatment, and/or alleviation of edema can be extended to any disease or condition where edema is a component, such as a disease or condition chosen among heart failure, liver cirrhosis, kidney diseases such as nephrotic syndrome, malnutrition, cancer, asthma, allergic rhinitis, COPD, acute lung injury, conditions involving the accumulation of exudate in the lung or lungs, ischemia, trauma and septic shock.

Among conditions involving the accumulation of exudate in the lung, the following conditions can be mentioned: plural efflusion of different etiology, lower respiratory tract infections, pneumonia, acute bacterial infections of the lung, tuberculosis, occupational lung diseases, mainly pneumoconiosis (chronic, fibrotic lung diseases caused by inhalation of inorganic dusts and particulate matter, e.g. asbestosis, silicosis) and hypersensitivity pneumonitis (allergic lung disease, such as an inflammation resulting from the inhalation of organic dusts, e.g. farmer's lung), lung damage resulting from exposure to radioactivity, etc.

In a method according to an embodiment of the invention, the oligonucleotide is administered in an amount of about 5 to about 500 μg per kg body weight, preferably in an amount of about 10 to 100 μg per kg body weight.

Other embodiments make available methods wherein the oligonucleotide is administered prophylactically, e.g. before an invasive surgical procedure, radiation therapy, hormone treatment, graft surgery and transplantation. The animal experiment shows that the compounds have a pronounced effect also when administered before the induction of edema.

The inventors also make available a method wherein the oligonucleotide is administered prophylactically, before an expected exposure to an irritant or an allergen. The compounds according to embodiments of the invention can thus be used for alleviating or preventing seasonal allergies, either alone or in combination with other conventionally used pharmaceuticals.

Another embodiment is a method wherein the oligonucleotide is administered in combination with anti-inflammatory medication, e.g. steroid medication.

Another embodiment is a method wherein the oligonucleotide is administered in combination with a diuretic drug.

Interestingly, it is contemplated that the anti-swelling or anti-edema effect achieved with the presently tested compounds could also be seen when administering other immunomodulatory compounds, structural variations thereof, such as branched oligonucleotides, dumb-bell shaped oligonucleotide constructs, glycine-linked oligonucleotide constructs and the like, comprising the sequences presented in Tables 1 and 2.

However, without wishing to be bound by any specific theory, the present inventors believe that the DNA-based oligonucleotides presented here exhibit higher specificity, improved efficacy against swelling or edema, and are better adapted for human, clinical use due to their specific sequences.

EXAMPLES

1. Effects on Murine Phorbol Acetate (Tetradecanoylphorbol 13-acetate, TPA) or Arachidonic Acid (AA) Induced Ear Edema of Experimental Oligonucleotide Compounds Given by Different Administration Schemes Materials and Methods
Chemicals
Tetradecanoylphorbol 13-acetate (TPA), CAS 16561-29-8, purity approx. 99% by TLC (Sigma-Aldrich Sweden AB, Stockholm, Sweden) was stored as a frozen dry powder. Dimethyl sulfoxide (DMSO), CAS 67-68-5, sterile filtered, Hybri-Max® (Sigma-Aldrich Sweden AB, Stockholm, Sweden). Acetone, analytical grade, CAS 67-64-1, Labora AB, Sollentuna, Sweden.

A stock solution of TPA was prepared by dissolving TPA in DMSO, 1 mg/mL, and was stored frozen at −80° C. For study B-E, a working solution was prepared with 200 μL of the TPA stock solution added to 800 μL acetone. The working solution was used the same day as it was prepared.

Arachidonic acid (AA), CAS 506-32-1, Batch 106K1432, oil, purity approx. 99% by TLC (Sigma-Aldrich Sweden AB, Stockholm, Sweden). Acetone, analytical grade, CAS 67-64-1, Labora AB, Sollentuna, Sweden.

A stock solution of AA was prepared by diluting AA in acetone, 4 mg/10 μL, and was stored frozen at −80° C. A final working solution, 1 mg/10 μL, in acetone was prepared. The working solution was used within one hour after preparation.

Test Compounds

In total, 15 compounds were tested in the TPA and/or AA experiments, see Table 1-3. The oligonucleotides were synthesized by biomers.net GmbH, Ulm, Germany and stored frozen at −20° C.

Formulation

The compounds were diluted to working concentration with PBS (Fluka, Sigma) at room temperature. The concentration was adjusted by aid of UV spectrophotometry (Smart-Spec® 3000, BIO-RAD, Hercules, USA) to 95% accuracy.

Animal Experiments and Dosage

Animals

Female and male, SPF NMRI/KS mice (InDex Pharmaceutical AB's own breeding stock of SPF NMRI mice, MTC, Karolinska Institutet, Stockholm, Sweden) or female BALB/cJ mice (The Jackson Laboratory, Bar Harbor, Me., USA). The animals were grouped and acclimatized for at least one week before entering experiment.

Housing

The animals were kept in rooms at 21° C., ±3° C., and with a relative humidity of 55%±15%. The ventilation system has been designed to give 10 air changes per hour. The room was illuminated to give a cycle of 12 hours light and 12 hours darkness. Light was on from 06:00 to 18:00 hours.

The mice were kept in transparent polycarbonate (Macrolone type III) cages (floor area: 810 cm$^2$) 8 in each cage.

Bedding

The bedding in the cages was Beekay bedding (B&K, Sollentuna, Sweden).

Environmental Enrichment

For environmental enrichment, the animals were given a supply of Sizzele Nest or Happy-Mat, (Scanbur A. S, Lellinger, Denmark)

Diet

A complete, pellet rodent diet, R36 (Laktamin AB, Stockholm, Sweden) was supplied ad libitum.

Drinking Water

The animals had free access to animal drinking bottles with domestic quality drinking water.

Animal Identification, Grouping and Treatment

Each cage was identified by a cage card marked with study number, group number, ethical approval number, sex and animal ear numbers. The animals were individually marked on the tail with transverse lines corresponding to the animals' number, using a permanent-ink felt pen. An illustration of the protocols used for the different treatments is outlined in Table 4. The compounds were tested according to the same protocols with necessary modifications.

TABLE 4

Table 4. Examples of protocols used in the experiments

| Study A Group | n | TPA i.p. injection | Day | Dose |
|---|---|---|---|---|
| 1 | 4 | PBS, control | 0 | — |
| 2 | 4 | IDX0920 | 0 | 50 μg |
| 3 | 4 | IDX0150 | 0 | 100 μg |
| 4 | 4 | IDX0955 | 0 | 100 μg |
| 5 | 4 | IDX0001 | 0 | 100 μg |
| Study B Group | n | TPA One single s.c. injection | Day | Dose |
| 1 | 4 | PBS, control | −4 | — |
| 2 | 4 | IDX0920 | −4 | 50 μg |
| 3 | 4 | IDX0150 | −4 | 100 μg |
| 4 | 4 | IDX0955 | −4 | 100 μg |
| 5 | 4 | IDX0001 | −4 | 100 μg |
| Study C Group | n | TPA One single s.c. injection | Day | Dose |
| 1 | 4 | PBS, control | −4 | — |
| 2 | 4 | IDX0920 | −4 | 50 μg |
| 3 | 4 | IDX0150 | −4 | 100 μg |
| 4 | 4 | IDX0955 | −4 | 100 μg |
| 5 | 4 | IDX0001 | −4 | 100 μg |
| Study D Group | n | TPA One single s.c. injection | Day | Dose |
| 1 | 4 | PBS, control | −2 | — |
| 2 | 4 | IDX0920 | −2 | 50 μg |
| 3 | 4 | IDX0150 | −2 | 100 μg |
| 4 | 4 | IDX0955 | −2 | 100 μg |
| 5 | 4 | IDX0001 | −2 | 100 μg |
| Study E Group | n | TPA One single s.c. injection | Day | Dose |
| 1 | 4 | PBS, control | 0 | — |
| 2 | 4 | IDX0920 | 0 | 50 μg |
| 3 | 4 | IDX0150 | 0 | 100 μg |
| 4 | 4 | IDX0955 | 0 | 100 μg |
| 5 | 4 | IDX0001 | 0 | 100 μg |
| Study F Group | n | TPA One single s.c. injection | Day | Dose |
| 1 | 4 | PBS, control | 0 | — |
| 2 | 4 | IDX0920 | 0 | 50 μg |
| 3 | 4 | IDX0150 | 0 | 50 μg |
| 4 | 4 | IDX0955 | 0 | 50 μg |
| 5 | 4 | IDX0001 | 0 | 50 μg |
| Study G Group | n | TPA One single s.c. injection | Day | Dose |
| 1 | 4 | PBS, control | 0, +2 h | — |
| 2 | 4 | IDX0920 | 0, +2 h | 50 μg |
| 3 | 4 | IDX0150 | 0, +2 h | 100 μg |
| 4 | 4 | IDX0955 | 0, +2 h | 100 μg |
| 5 | 4 | IDX0001 | 0, +2 h | 100 μg |
| Study H Group | n | TPA One single i.n. injection | Day | Dose |
| 1 | 4 | PBS, control | −4 | — |
| 2 | 4 | IDX0920 | −4 | 50 μg |
| 3 | 4 | IDX0150 | −4 | 100 μg |
| 4 | 4 | IDX0955 | −4 | 100 μg |
| 5 | 4 | IDX0001 | −4 | 100 μg |
| Study I Group | n | TPA One single i.n. injection | Day | Dose |

TABLE 4-continued

Table 4. Examples of protocols used in the experiments

| | | | | |
|---|---|---|---|---|
| 1 | 4 | PBS, control | 0 | — |
| 2 | 4 | IDX0920 | 0 | 50 µg |
| 3 | 4 | IDX0150 | 0 | 100 µg |
| 4 | 4 | IDX0955 | 0 | 100 µg |
| 5 | 4 | IDX0001 | 0 | 100 µg |

| Study J Group | n | TPA One single i.n. injection | Day | Dose |
|---|---|---|---|---|
| 1 | 4 | PBS, control | 0, +2 hours | — |
| 2 | 4 | IDX0920 | 0, +2 hours | 50 µg |
| 3 | 4 | IDX0150 | 0, +2 hours | 100 µg |
| 4 | 4 | IDX0955 | 0, +2 hours | 100 µg |
| 5 | 4 | IDX0001 | 0, +2 hours | 100 µg |

| Study K Group | n | TPA One single s.c. injection | Day | Dose |
|---|---|---|---|---|
| 1 | 4 | PBS, control | 0 | — |
| 2 | 4 | IDX0150 | 0 | 0.1 µg |
| 3 | 4 | IDX0150 | 0 | 1 µg |
| 4 | 4 | IDX0150 | 0 | 10 µg |
| 5 | 4 | IDX0150 | 0 | 100 µg |

| Study L Group | n | TPA One single i.n. injection | Day | Dose |
|---|---|---|---|---|
| 1 | 4 | PBS, control | 0 | — |
| 2 | 4 | IDX0526 | 0 | 0.1 µg |
| 3 | 4 | IDX0526 | 0 | 1 µg |
| 4 | 4 | IDX0526 | 0 | 10 µg |
| 5 | 4 | IDX0526 | 0 | 100 µg |

| Study M Group | n | TPA One single i.n. injection | Day | Dose |
|---|---|---|---|---|
| 1 | 4 | PBS, control | 0 | — |
| 2 | 4 | IDX0500 | 0 | 0.1 µg |
| 3 | 4 | IDX0500 | 0 | 1 µg |
| 4 | 4 | IDX0500 | 0 | 10 µg |
| 5 | 4 | IDX0500 | 0 | 100 µg |

| Study N Group | n | TPA One single i.n. injection | Day | Dose |
|---|---|---|---|---|
| 1 | 4 | PBS, control | 0 | — |
| 2 | 4 | IDX0500 | 0 | 0.005 µg |
| 3 | 4 | IDX0500 | 0 | 0.01 µg |
| 4 | 4 | IDX0500 | 0 | 0.1 µg |
| 5 | 4 | IDX0500 | 0 | 1 µg |

| Study O Group | n | TPA One single i.n. injection | Day | Dose |
|---|---|---|---|---|
| 1 | 4 | PBS, control | 0 | — |
| 2 | 4 | IDX0500 | 0 | 10 µg |
| 3 | 4 | IDX0500 | 0 | 100 µg |
| 4 | 4 | IDX0150 | 0 | 10 µg |
| 5 | 4 | IDX0150 | 0 | 100 µg |

Test Procedure
Dose Administration

Intraperitoneal (i.p.) injections were performed by giving 100 µL in the lower right quadrant of the abdomen. Subcutaneous injections were done with 100 µL in the neck region. Intranasal administration was performed by letting the mouse inhale droplets into the nostrils, total volume 40 µL. All administrations were done on non-anesthetized mice.

Induction of Edema

Both outer ears of a non-anesthetized mouse were washed with mild soap (Palmolive, Sweden) using a soft tooth brush, the ears were dried with tissue and cleaned with tissue soaked with acetone. After allowing the acetone to evaporate, TPA or AA was applied on both sides, 10 µL, on each side of the ear with care to cover the whole ear. The mouse was held for 20 seconds to allow the solvent to evaporate.

Pharmacological Treatment

Intraperitoneal injections were given in the lower right quadrant of the abdomen with the animal held in a supine position. Subcutaneous (s.c.) injections were given in the neck of the animals. Intranasal administrations were given to mice held in a slightly reclining position. With an adjustable micro-pipette 40 µL of the test substance was given in droplets on the nostrils and the mouse was allowed to aspirate at free will.

Clinical Signs

Each mouse was observed daily until killed. All signs of illness, health and any behavioural changes were recorded.

Clinical Parameters

The ears of non-anesthetized mice were measured at different time points for up to 96 hours after the TPA was administered, or up to 24 hours for the AA model. The first measurements were done before the edema was induced. The thickness was recorded with a spring loaded dial micrometer (Limit, Thickness Gauge, accuracy 0.01 mm, contact area Ø6 mm, Luna AB, Allingsås, Sweden) in triplicates at all time points per ear.

The average thickness for both ears on a mouse was calculated and compared to the average thickness of the ears at the starting time point. The value obtained at the start of the experiment was set as 100%. The peak values and area under the curve (AUC) values for the treatment groups were calculated and compared to the inflamed control group, treated with PBS (set as 100%), and expressed as a percentage change ($\Delta$% AUC).

Statistics

Student's t-test was used to calculate statistical significance (Excel Statistical Functions, Microsoft® Excel 2002, Microsoft Corp., Redmond, USA).

Area under the curve (AUC) with base line set as 100 was calculated using GraphPad Prism version 4.03 for Windows (GraphPad Software, San Diego Calif. USA, www.graphpad.com).

Results

The experimental protocol is illustrated by the examples given in Table 4. AUC reduction and P-values were calculated against the positive control (TPA or AA+PBS).

Study A

This study showed a reduction of edema when the inventive compounds were given i.p., with induction of edema started on day 0. In this experiment the control substance IDX0150 showed an almost complete remission of the inflammation and reduced AUC by −38.9%.

Study B

Study B investigated the prophylactic effect of the compounds when given s.c. 4 days before induction of edema. IDX0920, IDX0955 and IDX0001 showed a reduction of AUC with −19.3%, −22.7% and −16.3% respectively, however not statistically significant (NS). IDX0150 showed no reduction of AUC. Because of poor outcome due to large variation between measurements, this study was repeated (study C).

Study C

In a repeated study of study B, ODN's given s.c. 4 days before induction of edema, showed a reduction of AUC with −3%, −22%, −24.3% and −17.9% respectively, statistically significant for IDX0150 ($P<0.01$), IDX0955 ($P<0.01$) and IDX0001 ($P<0.05$).

Study D

In a shorter prophylactic regimen, given s.c., 2 days before induction of edema, almost similar results as in study C were obtained. Statistically significant for IDX0920, IDX0150, IDX0955 (P<0.01) and not significant for IDX0001. The reduction of AUC was −19.1%, −16.5%, −17.8% and −12.4% respectively.

Study E

In this study the compounds were given on the same day as edema was induced. Induction was staggered to allow for approximately 20 minutes waiting time for each mouse. In this study there was relatively uniform reduction of AUC, IDX0920 −19.4%, IDX0150 −27.3%, IDX0955 −17.7% and IDX0001 −16.7%. All compounds resulted in statistically significant reduction (P<0.01).

Study F

In this study, the compounds were given on the same day as the swelling was induced, at equal doses (50 μg) to each animal. This also resulted in reduction of AUC, IDX0920 −17%, IDX0150 −31.1%, IDX0955 −18.3% and IDX0001 −13.2%. Except for IDX0920 which showed a delayed downwards slope, all other compounds showed significant reduction of swelling, IDX0150 and IDX0955 with P<0.01 and IDX0001, with P<0.05.

Study G

To investigate a therapeutic regimen, the compounds were given 2 hours after induction of edema. This resulted in significant reduction of AUC in IDX0920 −43.8% (P<0.01), IDX0150 −42.3% (P<0.01) and IDX0955 −40.7% (P<0.05). IDX0001 showed a −17.9% reduction which was not statistically significant.

Study H

To study alternative administration routes, intranasal administration was investigated. In comparison to s.c. administration similar time-points and doses were chosen. In study H, intranasal administration was given, in a prophylactic protocol, 4 days before swelling was induced. This resulted in an effective reduction of swelling than what was obtained with s.c. administration. The reduction of AUC was, IDX0920 −33.8% (P<0.01), IDX0150 −25.7% (P<0.01), IDX0955 −17.4% (P<0.05) and IDX0001 −25.7% (P<0.05).

Study I

When intranasal administration was given on day 0, on the same day as edema was induced, effective reduction of swelling was found. Reduction of AUC was, IDX0920 −27.3% (P<0.01), IDX0150 −28.4% (P<0.01), IDX0955 −28.8% (P<0.05) and IDX0001 −6.4% (NS).

Study J

In the therapeutic protocol as used in study G, intranasal administration also resulted in a good reduction of swelling. AUC was shown to be reduced in IDX0920 with −28.7% (P<0.05), IDX0150 −28.8% (P<0.01), IDX0955 −17.2% (P<0.05) and IDX0001 −25.2% (P<0.05).

Study K

Dose response was investigated in studies K-O. In study K, 0.1, 1, 10 and 100 μg of IDX0150 was given. The result showed reduction of swelling in a dose-dependent manner. Reduction of AUC was; −13.9% (P<0.05) with 0.1 μg, −16.3% (P<0.05) with 1 μg, −27.9% (P<0.05) with 10 μg, and −45% (P<0.01) with 100 μg.

Study L

The negative control IDX0526, having the CpG motif substituted with a GC, was investigated in a dose response protocol similar to study K. It was found that there was no anti-swelling activity using IDX0526. Differences in AUC were; with 0.1 μg+1.24%, with 1 μg−1.24%, with 10 μg−0.26% and with 100 μg+6.18%, all no statistical significant changes.

Study M

To investigate the significance of the degree of phosphorothioate modification in the backbone of the oligonucleotide, a fully phosphorothioated oligonucleotide, IDX0500, was used. This compound showed statistically significant anti-swelling properties in all doses tested, with a reduction of AUC for; 0.1 μg−46.9%, 1 μg−41.3%, 10 μg−40.9% and 100 μg−59.1% (all P<0.01).

Study N

To further study the therapeutic window for IDX0500, study N was undertaken. The doses were 0.005 μg, 0.01 μg, 0.1 μg and 1 μg. The compound exhibited statistically significant effect in the doses 0.1 and 1 μg which was in agreement with study M. The reduction of AUC was; −15% for 0.005 μg (NS), −15.3% for 0.01 μg (NS), −18.2% for 0.1 μg (P<0.01), and −54.1% for 1 μg (P<0.01).

Study O

In this experiment, IDX0500 and IDX0150 were compared at equal doses of 10 and 100 μg given s.c. on day 0. Similar results were obtained between doses and the two compounds, showing statistically significant reduction of AUC for IDX0500; 10 μg gave −25.5%; 100 μg−39.9%, and for IDX0150 10 μg gave −25.5%; 100 μg−39.9% (all doses P<0.01).

In addition to the experiments done with the control compounds and IDX0001, all other test compounds were investigated in a similar fashion in the TPA and/or AA ear edema models, where the test compounds were given subcutaneously (10 μg) 20 minutes before induction of edema. The results were expressed as reduction of peak value and reduction of area under curve (AUC) in Table 5.

TABLE 5

Results obtained for the compounds tested
Table 5

| SEQ ID NO | IDX-No | Sequence 5'-3' | Peak reduction (%) TPA | Peak reduction (%) AA | AUC reduction (%) TPA | AUC reduction (%) AA |
|---|---|---|---|---|---|---|
| 1 | IDX9024 | T*G*C*CATTCGTCGTTCTCGTC*G*T*T | −30.9 | −14.4 | −47.3 | −58.5 |
| 2 | IDX9025 | T*G*C*CATTCGTCGATTTCGTC*G*A*T | −23.5 | −14.9 | −57.8 | −81.9 |

TABLE 5-continued

Results obtained for the compounds tested
Table 5

| SEQ ID NO | IDX-No | Sequence 5'-3' | Peak reduction (%) TPA | Peak reduction (%) AA | AUC reduction (%) TPA | AUC reduction (%) AA |
|---|---|---|---|---|---|---|
| 3 | IDX9038 | T*C*G*TCGTTCGGCCGATCG*T*C*C | −37.9 | ND | −47.4 | ND |
| 4 | IDX9053 | G*G*G*TCGTCTG*C*G*G | −30.5 | ND | −39.0 | ND |
| 5 | IDX9076 | T*C*C*CAAGATCGTCC*A*G*G | −2.6 | −20.1 | −5.1 | −45.7 |
| 6 | IDX9078 | T*C*C*GATCGTCC*A*G*G | −26.1 | −16.4 | −41.3 | −79.4 |
| 7 | IDX9087 | T*C*G*TCTGCTTAGTTCGTTA*G*T*T | +0.9 | ND | −40.2 | ND |
| 9 | IDX9051 | G*G*G*GCGTCTGCC*G*G*G | −29.5 | −17.7 | −54.0 | −67.5 |
| 10 | IDX9064 | T*C*C*ATGGTCAGGGTCCCGG*G*G*G | −41.7 | ND | −59.7 | ND |

ND = not done

Peak Values

Peak and AUC values were also compared in order to stratify the anti-swelling effectiveness of the different treatment schemes.

Discussion

The present experiments addressed extended prophylactic and therapeutic treatment regimens using intraperitoneal, subcutaneous and intranasal routes. In addition, the dose response was investigated using compounds IDX0150 and IDX0500 (SEQ ID NO 11 and 12, respectively).

The grade of edema can be followed by measuring the edema formation or swelling after topical TPA treatment of the outer ear in mice. This swelling normally peaks after 24 hours and then gradually subsides during one week.

All the AUC and peak values were found to be lower than the positive control. In most instances this reduction of swelling was statistically significant (P<0.05). However, in some experiments, statistically significant reduction was not reached. This has been observed in connection with low grade edema induction in the whole experiment as such. To avoid this, special care had been taken to optimize TPA dose and by using immunologically mature mice.

The ear edema can be studied by obtaining the peak value of TPA induced edema and by calculation of area under the curve (AUC) from all edema measurements. AUC thus represents both the induction and remission of the edema.

Calculating the average peak value from the ten IDX0150 experiments (FIG. 2), a very high statistical significant reduction in peak values was found (P<0.001).

Thus IDX0150 was used as a norm for comparisons with the other compounds in this study.

The anti-swelling effects of IDX0150 (0.1-100 μg) and IDX0500 (0.005-100 μg) showed a wide dose response range. The anti-swelling effect of IDX0150 given at different timepoints, calculated as peak value reduction, diminished in the order: 2 h>day −2>day 0>day −4.

AUC reduction, diminished in the order: 2 h>day 0>day −2>day −4. These results indicate that these compounds can be used both for prophylactic administration and for treatment after swelling has started. The very good results with intranasal administration show that mucosal administration is efficient for presenting oligonucleotide compounds to the immune system in the body.

Conclusion

The studies A-O collectively support the anti-swelling effect of the inventive compounds in the TPA-induced ear edema model in mice. These compounds are effective immunomodulating agents when given by intraperitoneal, subcutaneous and intranasal administration routes, and their efficacy to reduce edema was also proven in different prophylactic and therapeutic schemes as exemplified by IDX0150 in FIGS. 1-3. The anti-swelling effect of the compounds is not limited to a general inflammatory pathway, but can also down-regulate inflammation induced by AA which e.g. activates the prostaglandin system. All the test compounds SEQ ID NO 1-10, were able to reduce edema as shown in the TPA and/or AA model.

2. Nasal Administration of Immunomodulatory Oligonucleotide Test Substances in a Murine Model of Ovalbumin (OVA) Induced Airway Inflammation: a Comparison of Prophylactic- and Different Therapeutic Protocols Materials and Methods Animals Female Balb/c mice (8 weeks), obtained from B&K (Sollentuna, Stockholm, Sweden) were used in the experiment. The mice were fed with a complete pellet rodent diet, R36 (Laktamin AB, Stockholm, Sweden) and water of domestic drinking quality ad libitum. The animals were kept in animal rooms at 21° C.±3° C., and with a relative humidity of 55%±15%. The ventilation system was designed to give 10 air changes per hour. The room was illuminated to give a cycle of 12 hours light and 12 hours darkness. Light is on from 07:00 h to 19:00 h. The mice were kept in transparent polycarbonate (Macrolone type III) cages (floor area: 820 cm2), 5 in each cage. The bedding in the cages was 4HV Aspen bedding (Tapvei, Finland). Each cage was identified by a cage card marked with study number, group number, sex and animal numbers.

Sensitisation and Aerosol Challenge

Mice were sensitized intraperitoneally with 200 μL OVA/aluminium hydroxide gel (1:3) on day 0 and 12 (see FIG. 6). OVA (chicken egg albumin grade V, Sigma, St. Louis, Mo.) was dissolved in saline and mixed with aluminium hydroxide gel to a concentration of 50 µg/mL by rotation at 4° C. for 3 h. On days 23, 26, 30 and 33 (see FIG. 6), mice were challenged in the lungs by inhalation of aerosolized OVA for 30 minutes using a Batelle exposure chamber. Aerosols were generated by a compressed-air nebulizer (Collison 6-jet) at airflow 7.4 L/min using a nebulizer concentration of 10 mg/mL OVA dissolved in PBS (Sigma, St Louis, Mo., USA). The control group with non-sensitized animals received no other treatment than aerosolized OVA at days 23, 26, 30 and 33. There was also a control group of sensitized mice which did not receive aerosol challenge.

Oligonucleotides

In this OVA model (FIG. 6), a total of 4 oligonucleotides were tested, IDX9025, IDX9038, IDX9053 (Table 1, SEQ ID NO 2-4) and IDX0150 (Table 3, SEQ ID NO 11). The oligonucleotides were synthesized by biomers.net GmbH, Ulm, Germany and stored frozen at −20° C. The oligonucleotides were diluted with PBS to the working concentration (1,247 µg/µL) and kept at −20° C. until the first day of instillation, thereafter they were placed at 4° C.

Treatment of OVA Induced Airway Inflammation

In a first experiment, both prophylactic and therapeutic protocols were tested (see FIG. 6). The drug treatment consisted of intranasal instillations of IDX0150 (1,247 µg/µL, provided by InDex Pharmaceuticals AB, Stockholm, Sweden) on days 16 and 21 (prophylactic protocol), on days 30 and 33 (therapeutic protocol A) or on days 30 and 34 (therapeutic protocol B). The installations in the therapeutic protocols (A & B) on days 30 and 33 were given 4 h after aerosol challenge. The second installation in protocol B on day 34 was given 24 h after the last aerosol challenge. The drug was administered in 40 µL PBS giving a dose of ~50 µg/mice (49.88 µg/mice). The two sensitized sham-treatment groups were instilled with PBS, the same total volume as for the treatment groups, according to either the prophylactic protocol (days 16 and 21) or to the therapeutic protocol A (days 30 and 33).

TABLE 6

Table 6. Experimental groups in OVA induced airway inflammation

| Groups | n | OVA immunised | OVA aerosol | Treatment | Dose |
|---|---|---|---|---|---|
| 1 | 4 | No | Yes | PBS | — |
| 2 | 5 | Yes | Yes | 2x PBS prophylactic | — |
| 3 | 5 | Yes | Yes | IDX0150 prophylactic | 2x 50 µg |
| 4 | 5 | Yes | Yes | 2x PBS therapeutic A | — |
| 5 | 5 | Yes | Yes | IDX0150 therapeutic A | 2x 50 µg |
| 6 | 5 | Yes | Yes | IDX0150 therapeutic B | 2x 50 µg |
| 7 | 4 | Yes | No | PBS | — |

In a second experiment, since administration of IDX0150 in the first experiment using prophylactic protocol (FIG. 6) gave a significant reduction of airway inflammation (FIG. 7), three other substances were tested with the same protocol. The drug treatment consisted of intranasal instillations of IDX9025, IDX9038 and IDX9053 (Table 1) (1,247 µg/µL, provided by InDex Pharmaceuticals AB) on days 16 and 21 (see FIG. 6, prophylactic protocol). All substances were administered in 40 µL PBS giving a dose of ~50 µg/mice (49.88 µg/mice). The two sensitized sham-treatment groups were instilled with PBS, the same total volume as for the treatment groups, according to the prophylactic protocol (days 16 and 21).

Analysis of Airway Inflammation Parameters

Mice were killed by cervical dislocation 42 h after the last OVA aerosol challenge. The trachea was cannulated with polyethylene tubing (Becton Dickinson, Sparks, Md., USA) and bronchoalveolar lavage (BAL) was performed using 4×1 mL aliquots of ice-cold Hank's balanced salt solution (HBSS) (Sigma, St Louis, Mo., USA). The BAL fluid was centrifuged (400 g, 10 min, 4° C.) and the BAL fluid cells were resuspended in 0.4 mL PBS. The total number of leukocytes counted using tryphan blue exclusion in a Barker chamber. Duplicate Cytospin (Cytospin 3, Shandon, Runcorn, UK) preparations of BAL fluid cells were stained with May Grünewald Giemsa for differential counts, using standard morphological criteria.

Statistical Analysis

Statistical comparisons were performed using One-way analysis of variance (ANOVA) using Dunnett's post hoc correction to compare with sensitized PBS treated control mice (GraphPad Prism 3). Data are shown as mean±standard deviation. $P<0.05$ was considered significant.

Results

The ovalbumin induced allergic asthma model is a widely used model to reproduce the pulmonary inflammation found during asthma. The results obtained here, correlate to the swelling of the mucous membrane of the airways, and the results are thus a relevant measurement of the reduction of edema. Analysis of this model relies on general indicators of asthma such as BAL analysis where the type and amount of infiltrating inflammatory cells such as polymorphonuclear cells (PMN) are identified and counted.

Consequently, the BAL fluid cells derived from each mouse were counted as described and the values plotted as a combined histogram providing mean values for the different treatment groups (FIG. 7).

In general terms, the level of induced airway inflammation was high as indicated by a large influx of the 4 analyzed cell types into the lungs of the animals (PBS group) in both of the experiments. The control groups ("no aerosol", and "no challenge") demonstrated no signs of induced inflammation confirming that the animals did not exhibit a natural allergic response to the aerosol ovalbumin protein and that the ovalbumin protein used was not contaminated with, for example, LPS.

The complete absence of any signs of inflammation in the "no aerosol" control groups confirmed that the experimental procedure of OVA immunization itself did not induce lung inflammation.

Following nasal treatment in a prophylactic protocol when given twice, 7 and 2 days before challenge of inflammation, the test article IDX0150 was able to significantly reduce the migration of leukocytes and eosinophils into the BAL fluid ($P<0.05$ and $P<0.001$ respectively) (FIG. 7).

In the therapeutic arm of this protocol, when IDX0150 was given 7 and 11 days after challenge of inflammation, i.e. very late in the experimental period, there were no statistically proven effects.

Following nasal treatment in the second experiment (FIG. 8), the test substance IDX9038 was able to significantly reduce the migration of leukocytes ($P<0.05$) and eosinophils ($P<0.001$) into BALF fluid. IDX9025 and IDX9053 showed no significant reduction of cell migration into BALE fluid in this experiment.

Conclusions

This in vivo study affords the following conclusion: A statistically significant reduction in the number of leukocytes, eosinophils and lymphocytes infiltrating the BAL fluid was observed in animals when treated with the inventive compounds. In this model, it was more appropriate to measure inflammation, but the results are equally applicable to edema. Further, the study confirmed the suitability of nasal administration as an effective route.

3. Thioglycolate Induced Pleurisy in C57/Bl6 Mice

Materials and Methods

An animal model was set up to study the effect of oligonucleotides according to an embodiment of the present invention on cell migration and vascular permability.

Mice were anesthetized by an intraperitoneal injection of 0.15-0.20 ml of a mixture of ketamine (Ketalar® Parke-Davis; 25 mg/ml) and xylazine (Narcoxyl Vet.® Veterinaria AG; 5 mg/ml).

The left jugular vein was cannulated with polyethylene tubing (PE10) for intravenous administration (i.v.). A skin incision was made on the right side of the chest. Following dissection of the underlying muscle, pleurisy (inflammation of the lung sack) was induced by a single intrapleural injection of 100 µl of thioglycolate (Sigma). Sterile PBS was used as negative control.

FITC-conjugated dextran in PBS (100 µl, 30 mg/ml) was injected i.v. After 4 h, the animals were euthanized with an overdose of anaesthesia, the chest was carefully opened and the exudate was removed by aspiration and the volume noted. The thorax was then rinsed with 1 ml of ice-cold 3 mM EDTA in PBS. Exudate which was contaminated with red blood cells was discarded.

The exudate and rinsed material was centrifuged at 1500 g for 5 min and the supernatant was used for measurement of fluorescence intensity in a fluorometer (Fluoroskan Acsent, LabSystems) and clearance volume of FITC-dextran was calculated. The pellet was resuspended in PBS with 0.1% BSA for 15 min to block unspecific antibody binding. 10 µl of cell suspension was used for differential white blood cells (WBC) count in a Bürker chamber.

Cells from the exudate were stained with neutrophil and macrophage specific antibodies and were analyzed by flow cytometry (FACSort and CellQuest software, BD). Analysis included total white blood cell count, based on their typical appearances in the forward and side scatter. PMN and macrophages were further identified by their expression of Ly6G and F4/80, respectively.

In order to test the effect of oligonucleotides according to embodiments of the present invention, the compound to be tested was administered intraperitoneally, at a dose of 100 µl, i.e 50 µg/mouse, about 20 minutes before induction of pleurisy. In this study, the compound tested was IDX0150 (SEQ ID NO 11, Table 3).

Results

The thioglycolate induced pleurisy model is one of the models of choice for practical screening of new drugs under development although it is technically complicated and can show occasional individual disparate values. However, this model is restricted in the number animals that can be tested simultaneously.

The results showed that animals responded to the inflammation inducing agent, thioglycolate, by a high immigration of PMN into the pleural cavity. This cellular reaction was reflected in the accumulation of pleural edema seen as a high clearance volume. IDX0150 treatment reduced recruitment of PMN (42% reduction) after thioglycolate inflammation induction (FIG. 9a). Treatment with IDX0150 also demonstrated low level of vascular permeability (68.2% reduction) similar to PBS control (FIG. 9b). The results represent mean±SD.

Hu et al., (2008) investigated the contribution of transendothelial vesicular pathway to edema formation. The group showed that pulmonary vascular permeability can be induced by activation of PMNs adherent to the vessel wall, and the more severe edema was observed with the higher PMN number. The compounds according to embodiments of the present invention clearly show reduction of PMNs (FIGS. 7, 8, and 9a), and consequently a reduction of edema (FIG. 9b). Experiments using an anti-PMN antibody showed that the anti-PMN-ab could equally reduce PMN and edema to the similar levels as the inventive compounds (data not shown).

Conclusion

These results in the pleurisy animal model points to the fact that the compound has a preferable treatment profile suitable for further testing and drug development.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

REFERENCES

Guochang Hu, Stephen M. Vogel, David E. Schwartz, Asrar B. Malik, Richard D. Minshall. (2008) Intercellular Adhesion Molecule-1-Dependent Neutrophil Adhesion to Endothelial Cells Induces Caveolae-Mediated Pulmonary Vascular Hyperpermeability. Circ Res. 102:e120-e131.

A. Gennaro (Ed.), Remington's Pharmaceutical Sciences, 18th Edition, Mack Publishing Co., Easton, Pa., 1990

The invention claimed is:

1. An oligonucleotide compound comprising a sequence selected from the group consisting of SEQ ID NO 1, SEQ ID NO 2, SEQ ID NO 5, SEQ ID NO 6, SEQ ID NO 7, and SEQ ID NO 10.

2. The oligonucleotide compound according to claim 1, comprising a sequence selected from the group consisting of SEQ ID NO 1, SEQ ID NO 2, SEQ ID NO 5, SEQ ID NO 6, and SEQ ID NO 7.

3. The oligonucleotide compound according to claim 1, comprising a SEQ ID NO 10.

4. The oligonucleotide compound according to claim 1, wherein the total length of the oligonucleotide is between about 12 and about 30 bases.

5. The oligonucleotide according to claim 1, wherein said oligonucleotide is chemically modified.

6. The oligonucleotide according to claim 1, wherein at least one nucleotide has a phosphate backbone modification.

7. The oligonucleotide according to claim 6, wherein at least one nucleotide has a phosphate backbone modification and said phosphate backbone modification is a phosphorothioate or phosphorodithioate modification.

8. A method for the prevention, treatment, and/or alleviation of edema in an individual, comprising administering to the individual an oligonucleotide compound comprising a sequence selected from the group consisting of SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, and SEQ ID NO 10 in a dose effective to achieve one or several of modification of vascular permeability, inhibition of neutrophil migration/activation, inhibition or reduction of eosinophil migration, inhibition or reduction of leukocyte migration, and inhibition or reduction of lymphocyte migration.

9. The method according to claim 8, wherein the route of administration is buccal, oesophagal, gastric, mucosal, transdermal, subcutaneous, or intraperitoneal administration.

10. The method according to claim 8, wherein the mucosal administration is nasal administration, inhalation, ocular administration, rectal administration, oral administration, urogenital administration or vaginal administration.

11. The method according to claim 8, wherein the edema in the individual is linked to a disease selected from the group consisting of heart failure, liver cirrhosis, kidney diseases such as nephrotic syndrome, malnutrition, cancer, asthma, allergic rhinitis, acute lung injury, a lung disease involving the accumulation of exudate, COPD, ischemia, trauma and septic shock.

12. The method according to claim 8, wherein the oligonucleotide is administered in an amount of about 5 to about 500 μg per kg body weight.

13. The method according to claim 12, wherein the oligonucleotide is administered in an amount of about 10 to 100 μg per kg body weight.

14. The method of claim 8, wherein the oligonucleotide is administered prophylactically, before a procedure chosen from an invasive surgical procedure, radiation therapy, hormone treatment, graft surgery and transplantation.

15. The method of claim 8, wherein the oligonucleotide is administered prophylactically, before an expected exposure to an allergen.

16. The method of claim 8, wherein the oligonucleotide is administered in combination with anti-inflammatory medication.

17. The method according to claim 8, wherein the oligonucleotide compound comprises a sequence selected from the group consisting of SEQ ID NO 1, SEQ ID NO 2, SEQ ID NO 3, SEQ ID NO 4, SEQ ID NO 5, SEQ ID NO 6, and SEQ ID NO 7.

18. The method according to claim 8, wherein the oligonucleotide compound comprises a sequence selected from the group consisting of SEQ ID NO 8, SEQ ID NO 9, and SEQ ID NO 10.

19. The method of claim 8, wherein edema is defined as a disorder or dysfunction in interstitial fluid balance in an organ or tissue, linked to a condition selected from the group consisting of heart failure, liver cirrhosis, kidney diseases such as nephrotic syndrome, malnutrition, cancer, asthma, allergic rhinitis, COPD, ischemia, trauma and septic shock.

20. The method of claim 8, wherein said oligonucleotide is chemically modified.

21. The method of claim 8, wherein said oligonucleotide is chemically modified and at least one nucleotide has a phosphate backbone modification.

22. The method of claim 8, wherein said oligonucleotide is chemically modified through a phosphate backbone modification comprising a phosphorothioate or phosphorodithioate modification.

23. The oligonucleotide compound according to claim 1, comprising a sequence selected from the group consisting of SEQ ID NO 1 and SEQ ID NO 2.

24. An oligonucleotide compound consisting of a sequence selected from the group consisting of SEQ ID NO 1, SEQ ID NO 2, SEQ ID NO 4, SEQ ID NO 5, SEQ ID NO 6, SEQ ID NO 7, SEQ ID NO 8, SEQ ID NO 9, and SEQ ID NO 10.

25. The oligonucleotide compound according to claim 24, consisting of a sequence selected from the group consisting of SEQ ID NO 1 and SEQ ID NO 2.

26. The method of claim 8, wherein the oligonucleotide compound comprises a sequence selected from the group consisting of SEQ ID NO 1 and SEQ ID NO 2.

27. The method according to claim 8, wherein the oligonucleotide compound consists of a sequence selected from the group consisting of SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, and SEQ ID NO 10.

28. The method according to claim 27, wherein the oligonucleotide compound consists of a sequence selected from the group consisting of SEQ ID NO 1 and SEQ ID NO 2.

* * * * *